US011040128B1

(12) United States Patent
Lee

(10) Patent No.: US 11,040,128 B1
(45) Date of Patent: Jun. 22, 2021

(54) INTEGRATED MOTORIZED HEMODIALYZER

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 35 days.

(21) Appl. No.: 16/752,625

(22) Filed: Jan. 25, 2020

(51) Int. Cl.
*A61M 1/16* (2006.01)
*A61M 1/26* (2006.01)
*B01D 61/28* (2006.01)
*B01D 63/02* (2006.01)

(52) U.S. Cl.
CPC .......... *A61M 1/1623* (2014.02); *A61M 1/262* (2014.02); *B01D 61/28* (2013.01); *B01D 63/02* (2013.01); *A61M 2206/12* (2013.01)

(58) Field of Classification Search
CPC ................ A61M 1/1623; A61M 1/262; A61M 2206/12; B01D 63/02; B01D 61/28
See application file for complete search history.

(56) References Cited

U.S. PATENT DOCUMENTS

| | | | |
|---|---|---|---|
| 3,422,008 A | 1/1969 | McLain | |
| 3,536,611 A | 10/1970 | De Filippi et al. | |
| 3,616,928 A | 11/1971 | Rosenblatt | |
| 4,002,567 A | 1/1977 | Konno et al. | |
| 4,451,369 A | 5/1984 | Sekino et al. | |
| 4,666,469 A | 5/1987 | Krueger et al. | |
| 4,758,341 A | 7/1988 | Banner | |
| 5,263,924 A * | 11/1993 | Mathewson | B01D 63/02 604/6.14 |
| 5,830,370 A * | 11/1998 | Maloney, Jr. | B01D 63/02 210/780 |
| 6,379,618 B1 * | 4/2002 | Piplani | A61M 1/1629 422/45 |
| 6,641,731 B1 * | 11/2003 | Heilmann | B01D 46/0004 210/321.79 |
| 7,220,435 B2 * | 5/2007 | Dastidar | A61K 31/198 424/489 |
| 9,186,629 B2 | 11/2015 | Mahley et al. | |
| 2008/0199357 A1 * | 8/2008 | Gellman | A61M 1/1698 422/48 |
| 2008/0234623 A1 * | 9/2008 | Strauss | B01D 63/02 604/6.11 |

(Continued)

FOREIGN PATENT DOCUMENTS

| | | |
|---|---|---|
| JP | 0464737 B1 | 12/1994 |
| WO | 2014202710 A1 | 12/2014 |
| WO | 2018060510 A2 | 5/2018 |

*Primary Examiner* — Krishnan S Menon

(57) ABSTRACT

To enhance diffusive mass transfer of small molecules and convective clearance of middle molecules, the present invention provides a cylindrical hemodialyzer which comprises a blood compartment having a packed bundle of hollow fibers in a doughnut configuration on a radial cross-section, and a motorized dialysate compartment comprising a dialysate inlet motor having an external stator and an internal rotor connected to an axial spiral flow converter slidably inserted in a center of the packed bundle of the hollow fibers. The cylindrical hemodialyzer is configured to recirculate dialysate across the packed bundle of the hollow fibers propelled by the dialysate inlet motor. A dialysate outlet motor of the motorized dialysate compartment having an external stator and an internal rotor is configured to drain the dialysate and to control ultrafiltration by said cylindrical hemodialyzer.

20 Claims, 12 Drawing Sheets

(56) References Cited

U.S. PATENT DOCUMENTS

2010/0170850 A1     7/2010   Heilmann et al.
2016/0095969 A1*   4/2016   Maurer ............... A61M 1/1623
                                                                          422/48

* cited by examiner

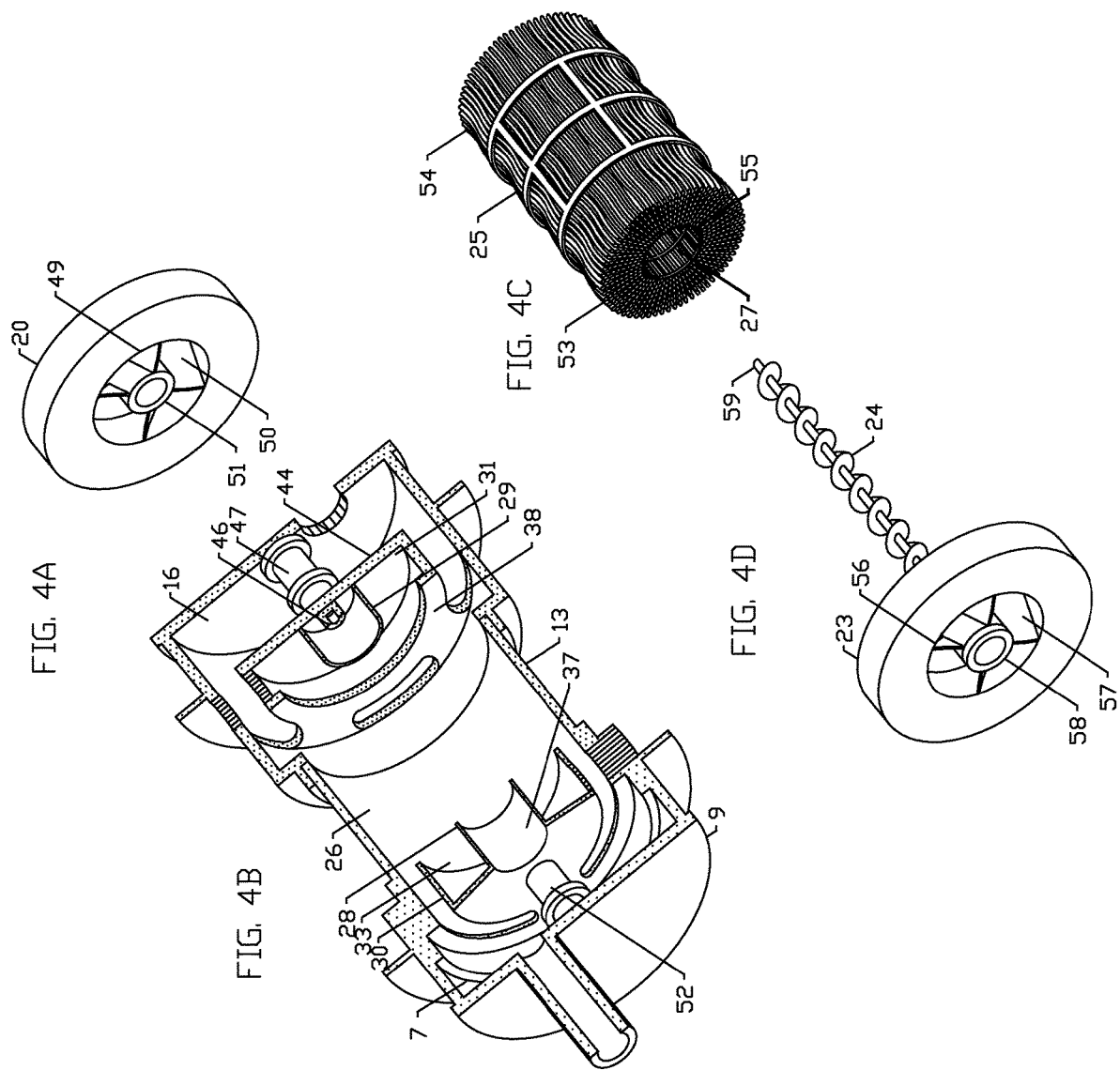

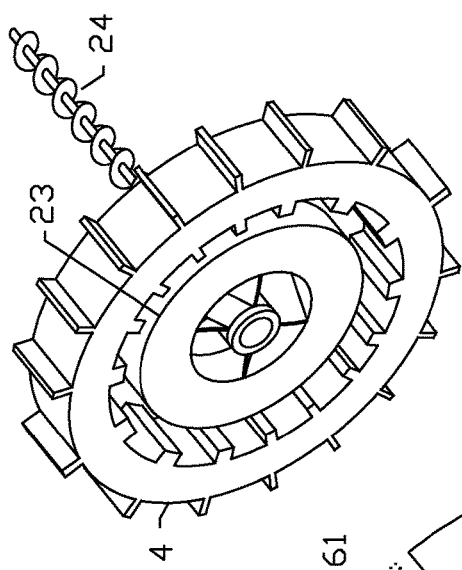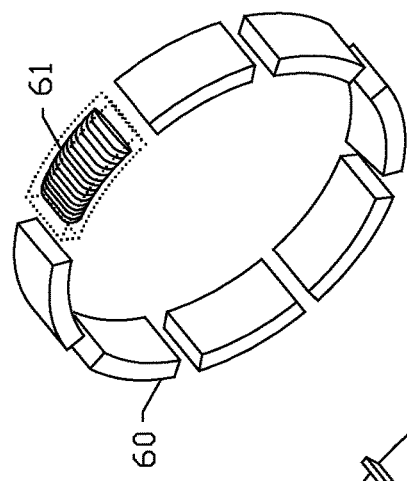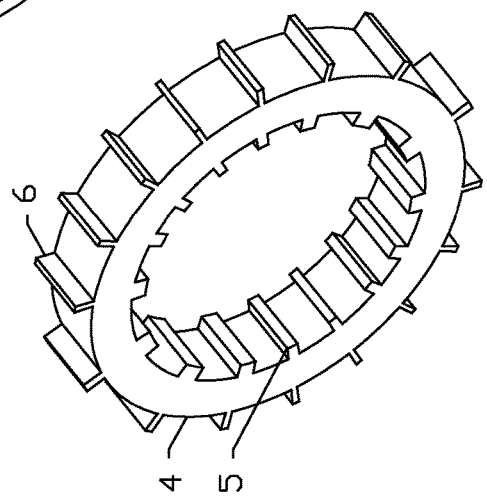

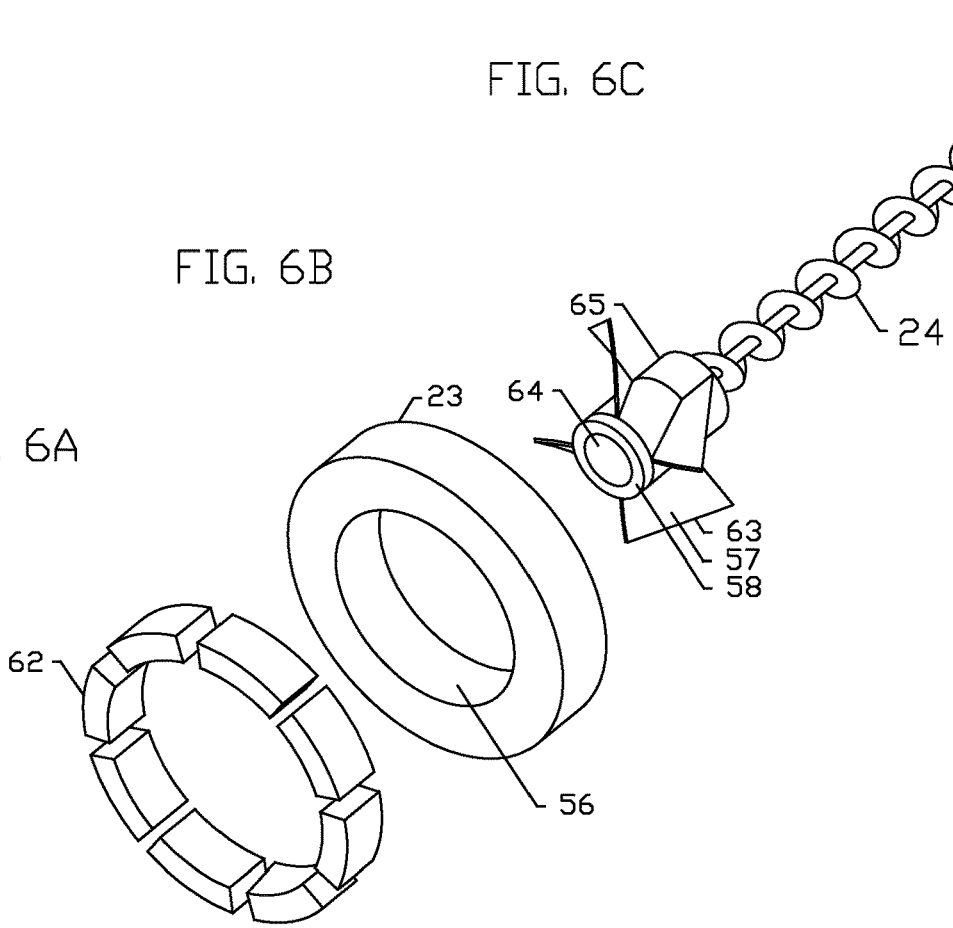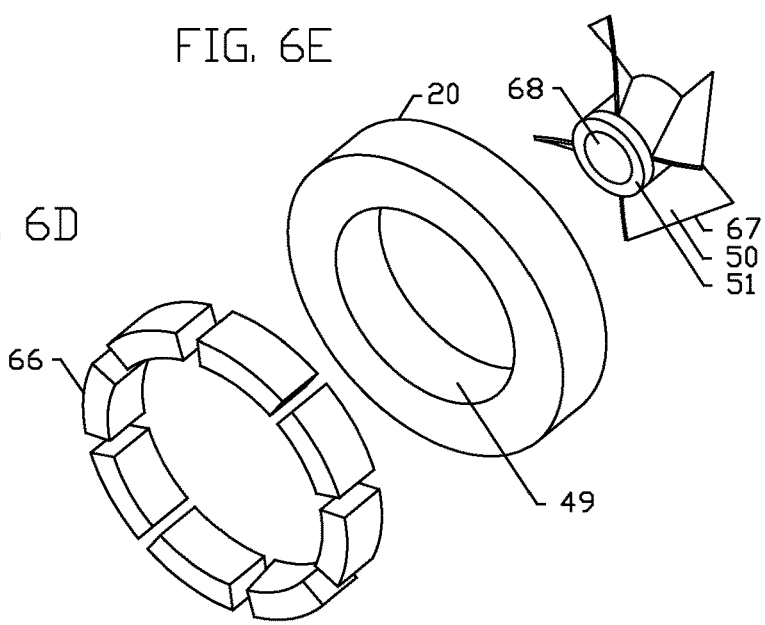

INTEGRATED MOTORIZED HEMODIALYZER

TECHNICAL FIELD

The present invention relates generally to the field of blood dialyzer. More specifically, the present invention provides a hemodialyzer for clinical hemodialysis for patients in renal failure.

BACKGROUND OF THE INVENTION

Hemodialysis has been successfully implemented to remove metabolic toxins from a patient whose kidney function no longer supports adequate clearance of the metabolic toxins from the patient's body. A critical component of the hemodialysis comprises hemodialyzer which removes the metabolic toxins mostly through diffusion of small molecule solutes and convection of middle molecules across a membrane of the hemodialyzer.

Efficiency of the hemodialyzer is known to depend on diffusive clearance of the small molecule solutes (KoA: mass transfer coefficient Ko x mass transfer area A), convective clearance of the middle molecules (Kuf: volume of fluid transferred across the membrane in mmHg of pressure gradient) and hydrostatic pressure gradient across the membrane of the hemodialyzer (TMP—TransMembrane Pressure). Of these, the diffusive clearance (diffusive mass transfer) appears to be limited by a dialysate phase in a way that the KoA increases proportionally to an increase in a dialysate flow rate but not to an increase in a blood flow rate. In a hemodialyzer system having a constant dialysate flow rate, and a fixed surface area and thickness of dialyzer membrane, the KoA is dependent on a concentration gradient between blood and dialysate, and on distribution of the blood in a blood compartment coaxially flowing in a countercurrent direction to the dialysate in a motorized dialysate compartment. It is well known that the efficiency of the hemodialyzer decreases when there is a mismatch between blood and dialysate flow distributions.

The majority of hemodialyzers in a cylindrical configuration available for clinical use have been found to have non-uniform blood distribution profiles between a central region and a peripheral region of a packed bundle of hollow fibers for a blood phase. Uniformity of blood distribution is inversely affected by concentration of red blood cells in the blood, wherein a higher concentration of the red blood cells in the blood phase is associated with a higher blood flow rate across and a higher wall shear stress on the hollow fibers located centrally than on those located peripherally in the packed bundle of the hollow fibers. For the dialysate phase, dialysate flow distribution and flow rate are affected by presence of irregularities in inter-fiber channels and gaps in a packing structure of the packed bundle of the hollow fibers. The packed bundle of the hollow fibers is more concentrated and more tightly packed in the central region than in the peripheral region of said packed bundle, resulting in a preferential distribution of dialysate flow and a greater dialysate flow rate in the peripheral region than in the central region which may harbor stagnant areas.

Decrease in the efficiency of a cylindrical hemodialyzer due to the non-uniform dialysate flow distribution and the non-uniform dialysate flow rate seen in a configuration of the coaxial countercurrent flow between the blood and the dialysate can be minimized by a specific configuration of the packing structure of the hollow fibers such as Moire structure. It can also be ameliorated by a change in configuration of the dialysate flow from the coaxial countercurrent flow to a centrifugal flow moving radially across the packed bundle of the hollow fibers from the central region to the peripheral region of the packed bundle. In the centrifugal flow configuration of the dialysate flow, the central region having the more densely packed bundle of the hollow fibers receives the dialysate at its highest flow rate which centrifugally decreases across a radius of the packed bundle toward the peripheral region. The central region of the packed bundle which has the highest concentration of the red blood cells in the blood phase receives the dialysate at its highest flow rate centrifugally moving away from an axis of the packed bundle, which exposes the blood phase in the central region to an increase in the dialysate flow rate. As indicated above, a regional KoA of the central region increases by the increase in the flow rate of the centrifugal dialysate flow, thus minimizing effects of the non-uniform blood distribution on the efficiency of the hemodialyzer.

Diffusive mass transfer of small molecules of a hemodialyzer has been studied to be limited by the dialysate phase in a way that KoA increases with increase in dialysate flow rate but not with increase in blood flow rate. Therefore, the limitation in efficiency of the hemodialyzer could be eliminated by the increase in the dialysate flow rate of a conventional hemodialyzer system using a fresh dialysate or by a recirculating dialysate system which is designed to overcome the limitation by recirculating a used dialysate to increase the dialysate flow rate. In either system, a key factor for the increase in the efficiency is the increase in the dialysate flow rate across a finite dimension (mass transfer area A) of a polymer membrane of the hollow fibers of the hemodialyzer.

Convective clearance of the middle molecules has been achieved by ultrafiltration using a hydrostatic pressure gradient across hemodialyzer having a large pore high-flux polymer membrane (hemodiafiltrator). Modeling studies suggest that 40%-50% of ultrafiltration rates contribute to the convective clearance, which can be achieved on 50% of plasma volume or up to one third of blood volume without exceeding a limit of TMP (Transmembrane pressure) of a particular high-flux polymer membrane. Control of the TMP for the ultrafiltration directly affects the efficiency of removal of the middle molecules. Since pressure of blood inside the hollow fibers is maintained relatively steady, the control of the TMP is mainly accomplished by changes in fluid pressure of the dialysate in the dialysate phase. In a typical hemodiafiltrator system, both the diffusive mass transfer of small molecules and the convective clearance of the middle molecules occur simultaneously on a session of hemodiafiltration. However, diffusion reduces concentration of the small molecules in blood, and decrease in the concentration of the small molecules reduces efficiency of removal of the small molecules by convection. On the other hand, the convection reduces available blood volume for the diffusion by removing the plasma volume.

Mutual exclusivity between the diffusion and the convection for the efficiency of the removal of the small molecules by a hemodiafiltrator may be ameliorated if the dialysate flow rate is made increase higher on a higher ultrafiltration rate, as the efficiency of the removal of the small molecules is dependent on the dialysate flow rate. The efficiency of the convection may not be affected much by changes in the dialysate flow rate as long as the hydrostatic pressure gradient across the packed bundle of the hollow fibers and an adequate plasma volume are steadily maintained. One way to maintain a balance between the diffusion and the convection for the efficiency of the removal of the small molecules is to control ultrafiltration rate of plasma volume by a feedback loop based on changes in the dialysate flow rate. Another way to compensate for a loss by the higher ultrafiltration rate in the efficiency of the diffusive mass transfer of the small molecules is to achieve a higher dialysate flow rate by recirculating the dialysate at a variable rate controlled by a positive feedback loop based on an increase in the ultrafiltration rate. The dialysate flow rate needs to be coordinated with the ultrafiltration rate which is dependent on the fluid pressure of the dialysate in the dialysate phase.

Achieving the higher flow rate of the dialysate to improve on the efficiency of the diffusive mass transfer as a single variable for the efficiency of the hemodialyzer system or as one of composite variables with the ultrafiltration rate for the convection in the hemodiafiltrator system may not be an insurmountable technical issue for a conventional stationary, in-center, hemodialysis or hemodiafiltration machine which could add larger capacity electric motors, a larger dialysate flow tubing system and a larger dialysate disposal system for the dialysate phase without such limiting factors as electricity consumption, dialysate volume, structural space, and number of structural components. These factors become a significant challenge for a portable dialysis system, or any dialysis system which would require considerations for these factors. Additionally, clinical studies on hemodialysis and hemodiafiltration have shown benefits of improved quality of life and significant decreases in mortality rates by applying a low ultrafiltration rate procedure (<10 ml/h per Kg of Body Weight) over extended hours (>6 hours) per session of hemodialysis. The extended-hours hemodiafiltration may not be readily applicable outside specialized dialysis centers using the hemodiafiltration system currently available which requires constant monitoring by trained nurses and significant hardware support. For an in-center hemodialysis/hemodiafiltration, a minimum number of the structural components for the hemodialysis/hemodiafiltration system include a conventional low-flux hemodialyzer or a high-flux hemodialyzer (hemodiafiltrator), a dialysate intake pump, a dialysate recirculating pump, a dialysate output pump, a dialysate flow tubing system connecting the aforementioned components to each other, a blood circulating pump, a blood flow tubing system and a command module. To overcome technical issues for at-home dialysis over the extended hours, I propose that a centrifugal-dialysate-flow hemodialyzer, the dialysate intake pump, the dialysate recirculating pump, and the dialysate output pump be assembled into one new hemodialyzer (or hemodiafiltrator depending on the pore size of a polymer membrane) which is made regulate its dialysate flow rate and ultrafiltration rate on its own upon receipt of commands from a command module. The new hemodialyzer comprises two motors, with the first motor for taking in and recirculating the dialysate and the second motor for draining the dialysate and controlling the ultrafiltration rate.

SUMMARY OF THE INVENTION

To enhance diffusive mass transfer of small molecules and convective clearance of middle molecules, the present cylindrical hemodialyzer comprises a blood compartment having a packed bundle of hollow fibers in a doughnut configuration on a radial cross-section, and a motorized dialysate compartment comprising a cylindrical tube in a configuration of a compartmentalized tubular cylinder, a dialysate inlet motor having a dialysate inlet external stator and a dialysate inlet internal rotor, and a dialysate outlet motor having a dialysate outlet external stator and a dialysate outlet internal rotor. The external stator is disposed outside the cylindrical tube and comprises a plurality of electric windings arranged in a circumferential configuration. The rotor is disposed inside the cylindrical tube and comprises a plurality of blocks of permanent magnet arranged in a circumferential configuration. The dialysate inlet internal rotor of the dialysate inlet motor is assembled with an axial spiral flow converter which is configured to be slidably inserted in a center of the packed bundle of the hollow fibers. The dialysate outlet internal rotor of the dialysate outlet motor is assembled with a distal axial propeller. The dialysate inlet motor is configured to propel and recirculate a dialysate centrifugally through and around the packed bundle of the hollow fibers. The axial spiral flow converter is configured to convert an axial dialysate flow in an open central tubular column of the packed bundle of the hollow fibers to a centrifugal dialysate flow across said packed bundle of the hollow fibers. The dialysate outlet motor is configured to drain the dialysate and to control ultrafiltration by regulating negative pressure generated by said dialysate outlet motor on the packed bundle of the hollow fibers.

In one embodiment, the packed bundle of the hollow fibers contains about 10,000 hollow fibers, with an inner diameter of each wet fiber measuring about 200 micrometer, a membrane thickness measuring about 20-45 micrometer, and a length measuring 80-240 mm. The hollow fibers are made of any of following polymers: Cuprophan, Cellulose diacetate, Cuproammonium rayon, Hemophan, Polysulfone, Polycarbonate, Cellulose triacetate, Polyamide, Polyethersulfone, Polyacrilonitrile, or Polymethylmethacrylate. An individual hollow fiber is configured in a tortuous longitudinal tube, wherein a maximum deviation (root) of a twist pitch of the individual hollow fiber from a longitudinal axis of the individual hollow fiber is less than a diameter of the individual hollow fiber. The configuration of the individual hollow fiber in the tortuous longitudinal tube is provided to establish intervening spaces between two adjacent individual hollow fibers, through which a dialysate flows at a substantially tangential angle to the individual hollow fibers. The configuration of the maximum deviation (root) of the twist pitch of the individual hollow fiber being less than the diameter of the individual hollow fibers is to avoid increasing impedance to a blood flow through a tortuous tubular configuration of the individual hollow fibers.

The packed bundle of the hollow fibers is provided in the doughnut configuration on a radial cross-section having an empty longitudinal column of the open central tubular column circumferentially surrounded by a plurality of the hollow fibers packed in a cylindrical configuration. A first set of resiliently stiff string harness in a tubular configuration is insertably placed inside the open central tubular column so as to provide said open central tubular column with a structural strength. A second set of elastomeric string harness in a tubular configuration is provided on an outer surface of a peripheral layer of the packed bundle of the hollow fibers to tie up said packed bundle of the hollow fibers. The elastomeric string harness is made of an elastomeric polymer, and is configured to be reversibly and circumferentially stretchable so as to let individual hollow fibers radially pushed apart from other adjacent individual hollow fibers by an outward pressure of the centrifugal dialysate flow from the open central tubular column to the peripheral layer of the packed bundle of the hollow fibers. The packed bundle of the hollow fibers is configured in a way that the dialysate radially flows from the open central tubular column of the packed bundle of the hollow fibers to the outer surface of the peripheral layer in a centrifugal direction.

In one embodiment, the hemodialyzer in the cylindrical configuration comprises a proximal dialyzer compartment, a mid tubular dialyzer compartment, and a distal dialyzer compartment, with each compartment having a cylindrical tubular space. The proximal dialyzer compartment comprises a dialysate inlet subcompartment distally adjoining a blood outlet subcompartment which is a part of the mid tubular dialyzer compartment. The dialysate inlet subcompartment comprises a tubular cylinder and a proximal radial wall. The proximal radial wall closes a proximal end of the dialysate inlet subcompartment. An inner diameter of the dialysate inlet subcompartment is larger than an outer diameter of the blood outlet subcompartment. A proximal portion of a tubular cylinder of the mid tubular dialyzer compartment adjoins a distal portion of the dialysate inlet subcompartment proximally. The mid tubular dialyzer compartment is provided in a tube-in-tube configuration with the blood outlet subcompartment on a proximal portion of said mid tubular dialyzer compartment. An inner diameter of the tubular cylinder of the mid tubular dialyzer compartment is larger than an outer diameter of a tubular cylinder of the blood outlet subcompartment. At an adjoined part between the portion of a tubular cylinder of the mid tubular dialyzer compartment and the distal portion of the dialysate inlet subcompartment, there is provided an upper radial wall separating the dialysate inlet subcompartment from the mid tubular dialyzer compartment. The upper radial wall comprises a plurality of upper curvilinear fenestrations disposed thereof around an outer perimeter of said upper radial wall. A radial width of a curvilinear fenestration is equivalent to a difference in distance between the inner diameter of the tubular cylinder of the mid tubular dialyzer compartment and the outer diameter of the blood outlet subcompartment. The dialysate inlet subcompartment is configured to communicate with a tubular lumen of the mid tubular dialyzer compartment through the plurality of the upper curvilinear fenestrations of the upper radial wall.

In one embodiment, the dialysate inlet subcompartment and the blood outlet subcompartment are compartmentalized without communication by the upper radial wall disposed between said dialysate inlet subcompartment and said blood outlet subcompartment. The dialysate inlet subcompartment comprises a first cylindrical space and is provided in a cylindrical tubular configuration having a proximal radial wall, a tubular side wall and the upper radial wall disposed distally. A dialysate intake tube adjoins the dialysate inlet subcompartment and opens to the first cylindrical space of the dialysate inlet subcompartment. Around a center of the upper radial wall disposed distally, a tubular opening coaxially adjoins the upper radial wall. The tubular opening is provided in a tubular configuration having a flush proximal end with the upper radial wall and a tubular cylinder of a length that goes through the blood outlet subcompartment and opens to the proximal portion of the mid tubular dialyzer compartment.

In one embodiment, the first cylindrical space of the dialysate inlet subcompartment coaxially encases the dialysate inlet internal rotor in a doughnut configuration which comprises the plurality of the blocks of permanent magnet housed in an outer cylindrical rim of said dialysate inlet internal rotor and a proximal axial propeller of the axial spiral flow converter fixedly attached to an inner surface of the outer cylindrical rim. The proximal axial propeller is a head portion of the axial spiral flow converter, and is coaxially connected with a stem portion of a longitudinal spiral blade. An outer surface of the tubular sidewall of the dialysate inlet subcompartment is slidably encircled by the dialysate inlet external stator which is configured to rotatably drive the dialysate inlet internal rotor. The dialysate inlet internal rotor is configured to rotatably propel the dialysate in the first cylindrical space into the open central tubular column of the packed bundle of the hollow fibers.

In one embodiment, the blood outlet subcompartment of the proximal dialyzer compartment comprises a second cylindrical space, provided in a cylindrical tubular configuration, having the upper radial wall of the dialysate inlet subcompartment, and a tubular side wall. The upper radial wall of the dialysate inlet subcompartment serves as an upper wall for the blood outlet subcompartment. The tubular sidewall is configured with a hole to accommodate a blood output tube. The blood output tube is provided in a tubular configuration, and fixedly connected to a hole of a tubular sidewall of the blood outlet subcompartment and opens to the second cylindrical space of the blood outlet subcompartment. The upper radial wall of the proximal dialyzer compartment comprises an outer tubular cylinder coaxially encircling an inner tubular cylinder protruding distally from said upper radial wall. The inner tubular cylinder is provided in a tubular configuration having a proximal tubular opening flush with the upper radial wall, and protrudes into and opens to the proximal portion of the mid tubular dialyzer compartment. A distal portion of the outer tubular cylinder is configured to leakproofly encase a proximal portion of a circumferential perimeter of the packed bundle of the hollow fibers housed in the mid tubular dialyzer compartment. The inner tubular cylinder runs for a length of the blood outlet subcompartment and opens to the proximal portion of the mid tubular dialyzer compartment. A distal portion of the inner tubular cylinder is configured to be leakproofly inserted in a proximal portion of the open central tubular column of the packed bundle of the hollow fibers in the doughnut configuration housed in the mid tubular dialyzer compartment. Difference in radial width between an inner diameter of the outer tubular cylinder and an outer diameter of the inner tubular cylinder is configured to be equivalent to a width from an edge of the open central tubular column to the peripheral layer of the packed bundle of the hollow fibers. An exposed proximal end of the packed bundle of the hollow fibers leakproofly encased by the distal portion of the inner tubular cylinder of the blood outlet subcompartment is open to the second cylindrical space of the blood outlet subcompartment, having a flush configuration with an inner surface of with the upper radial wall of the blood outlet subcompartment. The second cylindrical space of the blood outlet subcompartment collects the blood from a proximal end of the packed bundle of the hollow fibers, and transmits out the blood through the blood output tube.

In one embodiment, the mid tubular dialyzer compartment comprises the tubular cylinder as a third cylindrical space having the proximal portion, a distal portion and a mid portion connecting the proximal portion to the distal portion. The proximal portion of the mid tubular dialyzer compartment fixedly and leakproofly adjoins the distal portion of the dialysate inlet subcompartment, and comprises the blood outlet subcompartment coaxially disposed in the tube-in-tube configuration. The distal portion of the mid tubular dialyzer compartment fixedly and leakproofly adjoins and is communicated with a proximal portion of a dialysate outlet subcompartment of the distal dialyzer compartment. The mid tubular dialyzer compartment coaxially encloses the packed bundle of the hollow fibers in a way that there is provided an outer circumferential space bordered by the peripheral layer of the packed bundle of the hollow fibers and the inner surface of said mid tubular dialyzer compartment. The peripheral layer of the packed bundle of the hollow fibers is separated by >2 mm of a radial distance from the inner surface of said mid tubular dialyzer compartment. The outer circumferential space of the mid tubular dialyzer compartment is configured to communicate with the dialysate inlet subcompartment through the plurality of the upper curvilinear fenestrations of the upper radial wall of the dialysate inlet subcompartment, and with the dialysate outlet subcompartment through a plurality of lower curvilinear fenestrations of a lower radial wall of the dialysate outlet subcompartment.

In one embodiment, the distal dialyzer compartment comprises a dialysate outlet subcompartment compartmentally encircling a blood inlet subcompartment in a tube-in-tube configuration. The blood inlet subcompartment comprises a fourth cylindrical space, and the dialysate outlet subcompartment a fifth cylindrical space. A blood intake tube is fixedly attached to and opens to the fourth cylindrical space. A dialysate output tube is fixedly attached to and opens to the fifth cylindrical space. An inner diameter of a tubular cylinder of the dialysate outlet subcompartment is larger than an outer diameter of a tubular cylinder of the blood inlet subcompartment. A proximal portion of the tubular cylinder of the dialysate outlet subcompartment proximally adjoins the distal portion of the tubular cylinder of the mid tubular dialyzer compartment in an open tubular configuration, without a separating wall between the mid tubular dialyzer compartment and the dialysate outlet subcompartment. An inner diameter of a tubular cylinder of the dialysate outlet subcompartment is larger than an outer diameter of the tubular cylinder of the mid tubular dialyzer compartment. A proximal portion of the tubular cylinder of the blood inlet subcompartment is configured to leakproofly encase the distal portion of the circumferential perimeter of the packed bundle of the hollow fibers housed in the mid tubular dialyzer compartment.

In one embodiment, at an adjoined part between a proximal portion of a tubular cylinder of the blood inlet subcompartment and a proximal portion of the tubular cylinder of the dialysate outlet subcompartment, there is provided the lower radial wall separating the dialysate outlet subcompartment from the blood inlet subcompartment. The lower radial wall comprises the plurality of the lower curvilinear fenestrations disposed thereof around an outer perimeter of said lower radial wall. A radial width of a curvilinear fenestration is equivalent to a difference in distance between the inner diameter of the tubular cylinder of the dialysate outlet subcompartment and an outer diameter of the tubular cylinder of the blood inlet subcompartment. The dialysate outlet subcompartment is configured to communicate with the outer circumferential space of the mid tubular dialyzer compartment through the plurality of the lower curvilinear fenestrations. Blood flows from the blood inlet subcompartment of the distal dialyzer compartment to the blood outlet subcompartment of the proximal dialyzer compartment. Dialysate flows from the dialysate inlet subcompartment of the proximal dialyzer compartment through the mid tubular dialyzer compartment to the dialysate outlet subcompartment of the distal dialyzer compartment, which establishes a countercurrent flow configuration between dialysate flow and blood flow.

In one embodiment, the blood inlet subcompartment of the distal dialyzer compartment, provided in a cylindrical tubular configuration, comprises the lower radial wall of the dialysate outlet subcompartment, and a tubular sidewall. A tubular cylinder coaxially and fixedly adjoins an upper surface of the lower radial wall around a center of said upper surface of the lower radial wall. The tubular cylinder runs for a length of the blood inlet subcompartment and opens to the distal portion of the mid tubular dialyzer compartment. A proximal portion of the tubular cylinder is configured to be leakproofly inserted in a distal portion of the open central tubular column of the packed bundle of the hollow fibers in the doughnut configuration housed in the mid tubular dialyzer compartment. Disposed inside the tubular cylinder of the blood inlet subcompartment, an anchoring flange, provided in a configuration of tubular cylinder, coaxially and fixedly adjoins the upper surface of the lower radial wall around the center of said upper surface of the lower radial wall. A distal tip of the longitudinal spiral blade of the axial spiral flow converter is rotatably housed in a tubular cylinder of the anchoring flange. The tubular sidewall of the blood inlet subcompartment is configured with a hole to accommodate the blood intake tube. The blood intake tube is provided in a tubular configuration, and fixedly connected to the hole of the tubular sidewall of the blood inlet subcompartment. An exposed distal end of the packed bundle of the hollow fibers leakproofly encased by the proximal portion of the tubular cylinder of the blood inlet subcompartment is open to the fourth cylindrical space of the blood inlet subcompartment. The blood is pushed into the fourth cylindrical space through the blood intake tube, following which the blood goes through individual hollow fibers of the packed bundle of the hollow fibers from the distal portion to the proximal portion of the said packed bundle of the hollow fibers into the blood outlet subcompartment of the proximal dialyzer compartment. It then goes out through the blood output tube.

In one embodiment, the axial spiral flow converter comprises the head portion having the proximal axial propeller fixedly adjoining the stem portion of the longitudinal spiral blade along a longitudinal axis of the axial spiral flow converter. The proximal axial propeller comprises a plurality of helical blades fixedly attached to a rotary shaft at an angle ranging from 0°< to <180° degree. The proximal axial propeller is fixedly attached to the inner surface of the cylindrical rim of the dialysate inlet internal rotor which is rotatably housed in the first cylindrical space of the dialysate inlet subcompartment in a way that the proximal axial propeller is rotatable about a longitudinal axis of the cylindrical hemodialyzer and that the proximal axial propeller attached to the dialysate inlet internal rotor is rotatably propelled by the dialysate inlet external stator. The longitudinal spiral blade comprises a longitudinal shaft to which a single helical blade fixedly encircles said longitudinal shaft from a bottom of the proximal axial propeller to the distal tip portion of the longitudinal spiral blade. The longitudinal spiral blade is slidably and coaxially placed in the inner tubular cylinder of the blood outlet subcompartment, in the open central tubular column of the packed bundle of the hollow fibers for its entire length, and in the tubular cylinder of the blood inlet subcompartment. The distal tip of the longitudinal spiral blade is rotatably housed in the tubular cylinder of the anchoring flange of blood inlet subcompartment.

In one embodiment, the dialysate flows into the first cylindrical space of the dialysate inlet subcompartment through the dialysate intake tube, and is propelled into the open central tubular column of the packed bundle of the hollow fibers by the proximal axial propeller of the axial spiral flow converter. The proximal axial propeller coaxially rotates the longitudinal spiral blade which then centrifugally converts an axial flow of the dialysate coming into the open central tubular column of the packed bundle of the hollow fibers to a radial flow toward the outer circumferential space bordered by the peripheral layer of the packed bundle of the hollow fibers and an inner surface of the mid tubular dialyzer compartment. The dialysate collected in the outer circumferential space then flows to the fifth cylindrical space of the dialysate outlet subcompartment of the distal dialyzer compartment through the lower curvilinear fenestrations of the lower radial wall between the mid tubular dialyzer compartment and the dialysate outlet subcompartment. The dialysate collected in the fifth cylindrical space of the dialysate outlet subcompartment from the outer circumferential space of the mid tubular dialyzer compartment then flows out through the dialysate output tube by rotation of the dialysate outlet internal rotor of the dialysate outlet motor.

In one embodiment, the dialysate outlet subcompartment rotatably encloses the dialysate outlet internal rotor of the dialysate outlet motor which is configured to rotatably propel the dialysate out from the fifth cylindrical space into the dialysate output tube. A distal axial propeller is fixedly attached to an inner surface of a cylindrical rim of the dialysate outlet internal rotor which is rotatably housed in the fifth cylindrical space of the dialysate outlet subcompartment in a way that the distal axial propeller is rotatable about the longitudinal axis of the cylindrical hemodialyzer and that the distal axial propeller attached to the dialysate outlet internal rotor is rotatably propelled by the dialysate outlet external stator of the dialysate outlet motor. An outer surface of an outer tubular sidewall of the dialysate outlet subcompartment is slidably encircled by the dialysate outlet external stator which is configured to rotatably drive the dialysate outlet internal rotor.

In one embodiment, the dialysate inlet motor and the dialysate outlet motor are electrically driven, and identical to each other for the external stator, the internal rotor, the axial propeller attached to the inner surface of the cylindrical rim of the internal rotor, intake volume per rpm (revolution per minute), output volume per rpm, and rotational torque per rpm. The rotation speed of the dialysate inlet internal rotor governs a rate of dialysate intake through the dialysate intake tube into the cylindrical hemodialyzer. The rotation speed of the dialysate outlet internal rotor governs a rate of drainage of the dialysate from the cylindrical hemodialyzer through the dialysate output tube. The dialysate outlet motor is configured to control ultrafiltration across the packed bundle of the hollow fibers by varying rotation speed of the dialysate outlet internal rotor in relation to a rotation speed of the dialysate inlet internal rotor of the dialysate inlet motor. If the rotation speed of the dialysate outlet internal rotor is faster than that of the dialysate inlet internal rotor, it generates a negative pressure inside the cylindrical hemodialyzer. The negative pressure translates to an ultrafiltration pressure on the hollow fibers of the packed bundle of the hollow fibers. Differences in the rotation speed between the proximal and the dialysate outlet internal rotors while the rotation speed of the dialysate outlet internal rotor is maintained higher than that of the dialysate inlet internal rotor are configured to control a rate of the ultrafiltration. The proximal and dialysate outlet motor s are configured to be under a different set of commands from an electronic command module, respectively.

In one embodiment, the dialysate inlet internal rotor is configured to be axially movable up and down inside the dialysate inlet subcompartment along the longitudinal axis of the cylindrical hemodialyzer. The dialysate inlet internal rotor comprises a rotor center, provided in a tubular configuration, which is disposed at a center of the central helical spiral of the axial spiral flow converter. A cylindrical rod axially protruding from a center of an undersurface of a proximal radial wall in a distal direction is slidably inserted in the rotor center which is configured to rotate about the cylindrical rod. The cylindrical rod comprises a circular flange fixedly encircling the cylindrical rod, wherein the circular flange is disposed close to the undersurface of the proximal radial wall. The rod center is configured to slidably move up and down for a length over the cylindrical rod. Similarly, the distal tip of the longitudinal spiral blade of the axial spiral flow converter housed in the tubular cylinder of the anchoring flange in the blood inlet subcompartment is configured to slidably move up and down inside the tubular cylinder of the anchoring flange for the length. A rotating dialysate inlet internal rotor is configured to be slidably pushed up inside the dialysate inlet subcompartment by a dialysate flow upwardly returning from the outer circumferential space of the mid tubular dialyzer compartment to the dialysate inlet subcompartment, under a condition that the dialysate output tube no longer drains the dialysate out from the dialysate outlet subcompartment.

In one embodiment, the dialysate inlet subcompartment comprises a lower circumferential rim inwardly protruding from an inner surface of a tubular sidewall of said dialysate inlet subcompartment, immediately above the upper radial wall separating the dialysate inlet subcompartment from the mid tubular dialyzer compartment. A diameter of the lower circumferential rim of the dialysate inlet subcompartment is configured to slidably accommodate the dialysate inlet internal rotor in a way that there is a radial gap of equal to or greater than 2 mm between an outer perimeter of the dialysate inlet internal rotor and an inner surface of the lower circumferential rim. A height of the lower circumferential rim from the upper radial wall separating the dialysate inlet subcompartment from the mid tubular dialyzer compartment is configured to be shorter than the length of the axial movement of the dialysate inlet internal rotor inside the dialysate inlet subcompartment. By engaging/disengaging with the lower circumferential rim, the dialysate inlet internal rotor is configured to serve as a reversible valve for the dialysate flow: 1) the dialysate inlet internal rotor substantially blocks off the upper curvilinear fenestrations of the upper radial wall, thereby blocking off the dialysate flow moving from the dialysate inlet subcompartment to the outer circumferential space through the upper curvilinear fenestrations of the upper radial wall under a condition that the dialysate output tube drains the dialysate out from the dialysate outlet subcompartment and the dialysate inlet internal rotor is lowered down in the dialysate inlet subcompartment; 2) the dialysate inlet internal rotor opens up so as to allow the dialysate flow to move from the outer circumferential space to the dialysate inlet subcompartment through the upper curvilinear fenestrations of the upper radial wall under a condition that the dialysate output tube does not drain the dialysate out from the dialysate outlet subcompartment and the dialysate inlet internal rotor is pushed up in the dialysate inlet subcompartment. At a time that the dialysate output tube drains the dialysate out from the dialysate outlet subcompartment, the dialysate inlet internal rotor stays lowered inside the lower circumferential rim of the dialysate inlet subcompartment toward the upper radial wall separating the dialysate inlet subcompartment from the mid tubular dialyzer compartment. At a time that the dialysate output tube does not drain the dialysate out from the dialysate outlet subcompartment, the dialysate inlet internal rotor is uplifted out of the lower circumferential rim by the dialysate flow upwardly returning from the outer circumferential space to the dialysate inlet subcompartment through the upper curvilinear fenestrations of the upper radial wall, thereby opening up a channel from the outer circumferential space to the dialysate inlet subcompartment.

In one embodiment, the dialysate inlet internal rotor of the dialysate inlet motor is configured to recirculate the dialysate from the dialysate inlet subcompartment through the outer circumferential space then back to the dialysate inlet subcompartment. Full recirculation of the dialysate inside the cylindrical hemodialyzer requires three steps of procedures: 1) the dialysate intake to the cylindrical hemodialyzer be halted by blocking inflow of the dialysate to the dialysate intake tube; 2) the dialysate outlet internal rotor of the dialysate outlet motor be stopped so as to stop draining the dialysate out from the cylindrical hemodialyzer; 3) the dialysate inlet internal rotor of the dialysate inlet motor continues to rotate. Sequence of the full recirculation goes as follows: 1) the dialysate in the dialysate inlet subcompartment is propelled by the dialysate inlet internal rotor into the open central tubular column of the packed bundle of the hollow fibers: 2) the dialysate inside the open central tubular column of the packed bundle of the hollow fibers is centrifugally pushed across the packed bundle of the hollow fibers into the outer circumferential space inside the mid tubular dialyzer compartment; 3) the dialysate in the outer circumferential space is pulled back to the dialysate inlet subcompartment through the plurality of the upper curvilinear fenestrations of the upper radial wall between the mid tubular dialyzer compartment and the dialysate inlet subcompartment. Under the aforementioned configuration and a limited supply of the dialysate through the dialysate intake tube to the cylindrical hemodialyzer, partial recirculation can be achieved by rotation of the dialysate outlet internal rotor of the dialysate outlet motor at a rate of the rotation speed below a rate of the rotation speed of the dialysate inlet internal rotor. Thus, the present cylindrical hemodialyzer can recirculate the dialysate from 0% to 100% of the dialysate taken into said cylindrical hemodialyzer. For one scenario for the partial recirculation, an amount of the dialysate intake equals to an amount of the dialysate output. In a different setting whereby there is no supply of the dialysate through the dialysate intake tube to the cylindrical hemodialyzer, the rotation of the dialysate outlet internal rotor of the dialysate outlet motor at a rate of the rotation speed below a rate of the rotation speed of the dialysate inlet internal rotor produces both the partial recirculation and the ultrafiltration simultaneously. In this scenario, the partial recirculation is achieved on an ultrafiltrated plasma liquid which is subject to recirculation by the dialysate inlet motor. Therefore the present cylindrical hemodialyzer can achieve the ultrafiltration at a rate from 0% to a maximum percentage allowed for the cylindrical hemodialyzer while maintaining the recirculation from 0% to 100% of the dialysate.

In one embodiment, a metallic ink comprising particulated metal such as copper or aluminum is sprayed as a coating to an outer surface of the mid tubular dialyzer compartment, an outer surface of a proximal circumferential wing encircling a proximal portion of the mid tubular dialyzer compartment, and an outer surface of a distal circumferential wing encircling a distal portion of the mid tubular dialyzer compartment. The metallic ink comprising particulated metal such as copper or aluminum is configured to shield radiofrequency electromagnetic radiation generated from the dialysate inlet external stator and the dialysate outlet external stator to a level below 0.0001 µW/cm² to the packed bundle of the hollow fibers, so as to limit or eliminate an exposure of blood going through the packed bundle of the hollow fibers to the radiofrequency electromagnetic radiation.

BRIEF DESCRIPTION OF THE DRAWINGS

FIGS. 4A-4D depict a schematic three dimensional view of individual internal components.

FIGS. 5A-5C show a schematic illustration of individual components of a dialysate inlet motor.

FIGS. 6A-6C show a schematic view of individual components of a dialysate inlet internal rotor assembly comprising an axial spiral flow converter; FIGS. 6D-6F shows a schematic view of individual components of a dialysate outlet internal rotor assembly.

DETAILED DESCRIPTION OF THE DRAWINGS

Figure 1:
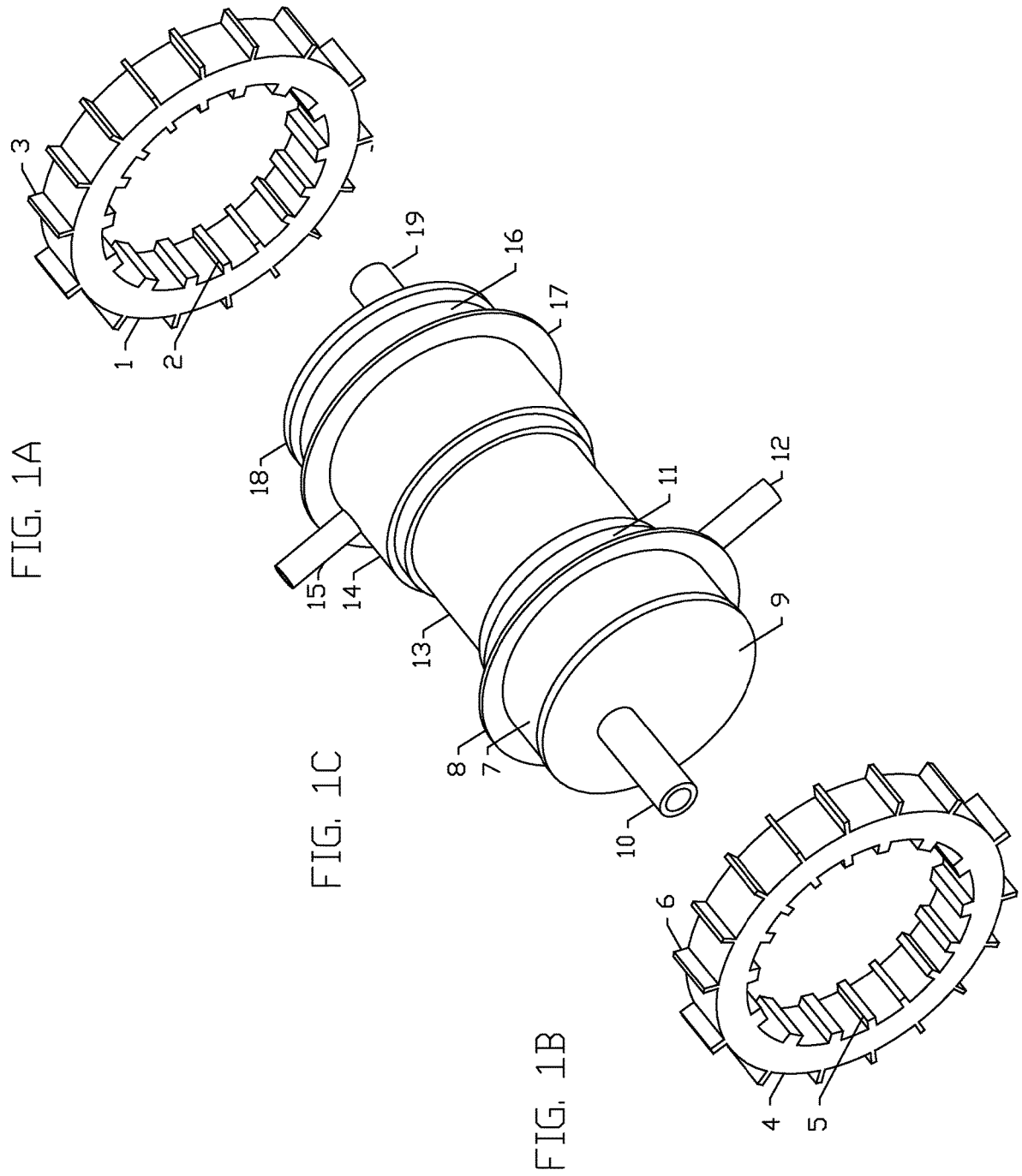
FIG. 1 shows a schematic three-dimensional view of an integrated motorized hemodialyzer comprising a cylindrical hemodialyzer and two external stators.

As described below, the present invention provides an integrated motorized hemodialyzer comprising a blood compartment having a packed bundle of hollow fibers in a doughnut configuration on a radial cross-section, a motorized dialysate compartment having a dialysate inlet motor with an axial spiral flow converter slidably inserted in a center of the packed bundle of the hollow fibers and a dialysate outlet motor with a helical spiral housed in a dialysate collection chamber, and a recirculatory conduit disposed inside the motorized dialysate compartment. It is to be understood that the descriptions are solely for the purposes of illustrating the present invention, and should not be understood in any way as restrictive or limited. Embodiments of the present invention are preferably depicted with reference to FIGS. 1 to 12, however, such reference is not intended to limit the present invention in any manner. The drawings do not represent actual dimension of devices, but illustrate the principles of the present invention.

FIGS. 1A-1C show a schematic three-dimensional illustration of the integrated motorized hemodialyzer. FIG. 1A shows a dialysate outlet external stator 1 of the dialysate outlet motor provided in a cylindrical configuration comprising a plurality of inner pins 2 and a plurality of outer pins 3 for air cooling of said dialysate outlet external stator 1. The dialysate outlet external stator 1 is configured to be slidably assembled over a distal portion 16 of a dialysate subcompartment shown in FIG. 1C. A dialysate inlet external stator 4 shown in FIG. 1B in a cylindrical configuration comprises a plurality of inner pins 5 and a plurality of outer pins 6 for the air cooling of said dialysate inlet external stator 4. The dialysate inlet external stator 4 is configured to be slidably assembled over a dialysate inlet subcompartment 7 shown in FIG. 1C. A hemodialyzer shown in FIG. 1C, provided in a cylindrical configuration, comprises the dialysate inlet subcompartment 7, a proximal portion 11 of a mid tubular dialyzer compartment 13, a proximal portion 14 of the dialysate outlet subcompartment located distal to the mid tubular dialyzer compartment 13, and the distal portion 16 of said dialysate subcompartment. The dialysate inlet subcompartment 7 is configured with a proximal radial wall 9 and a proximal circumferential wing 8, wherein the proximal radial wall 9 and the proximal circumferential wing 8 are configured to fasten in place the dialysate inlet external stator 4 encircling the dialysate inlet subcompartment 7. A dialysate intake tube 10 adjoins the proximal radial wall 9 and opens to the dialysate inlet subcompartment 7. A blood output tube 12 adjoins the proximal portion 11 of the mid tubular dialyzer compartment 13 and opens to a blood outlet subcompartment (not shown) inside said proximal portion 11. The distal portion 16 of the dialysate outlet subcompartment is configured with a distal radial wall 18 and a distal circumferential wing 17, wherein the distal radial wall 18 and the distal circumferential wing 17 are configured to fasten in place the dialysate outlet external stator 1 encircling the distal portion 16 of the dialysate outlet subcompartment. A dialysate output tube 19 adjoins the distal radial wall 18 and opens to the distal portion 16 of the dialysate outlet subcompartment. A blood intake tube 15 adjoins and opens to a blood inlet subcompartment (not shown) disposed inside the proximal portion 14 of the dialysate outlet subcompartment.

A metallic ink coating comprising particulated metal such as copper or aluminum is sprayed to an outer surface of the mid tubular dialyzer compartment 13, an outer surface of the proximal circumferential wing 8 facing the mid tubular dialyzer compartment 13, and an outer surface of the distal circumferential wing 17 facing the mid tubular dialyzer compartment 13. The metallic ink comprising particulated metal such as copper or aluminum is configured to reduce radiofrequency electromagnetic radiation generated from the dialysate inlet external stator 4 and the dialysate outlet external stator 1 to a level below 0.0001 $\mu W/cm^2$ to the packed bundle of the hollow fibers encased inside the mid tubular dialyzer compartment 13, so as to limit or eliminate an exposure of blood going through the packed bundle of the hollow fibers to the radiofrequency electromagnetic radiation.

Figure 2:
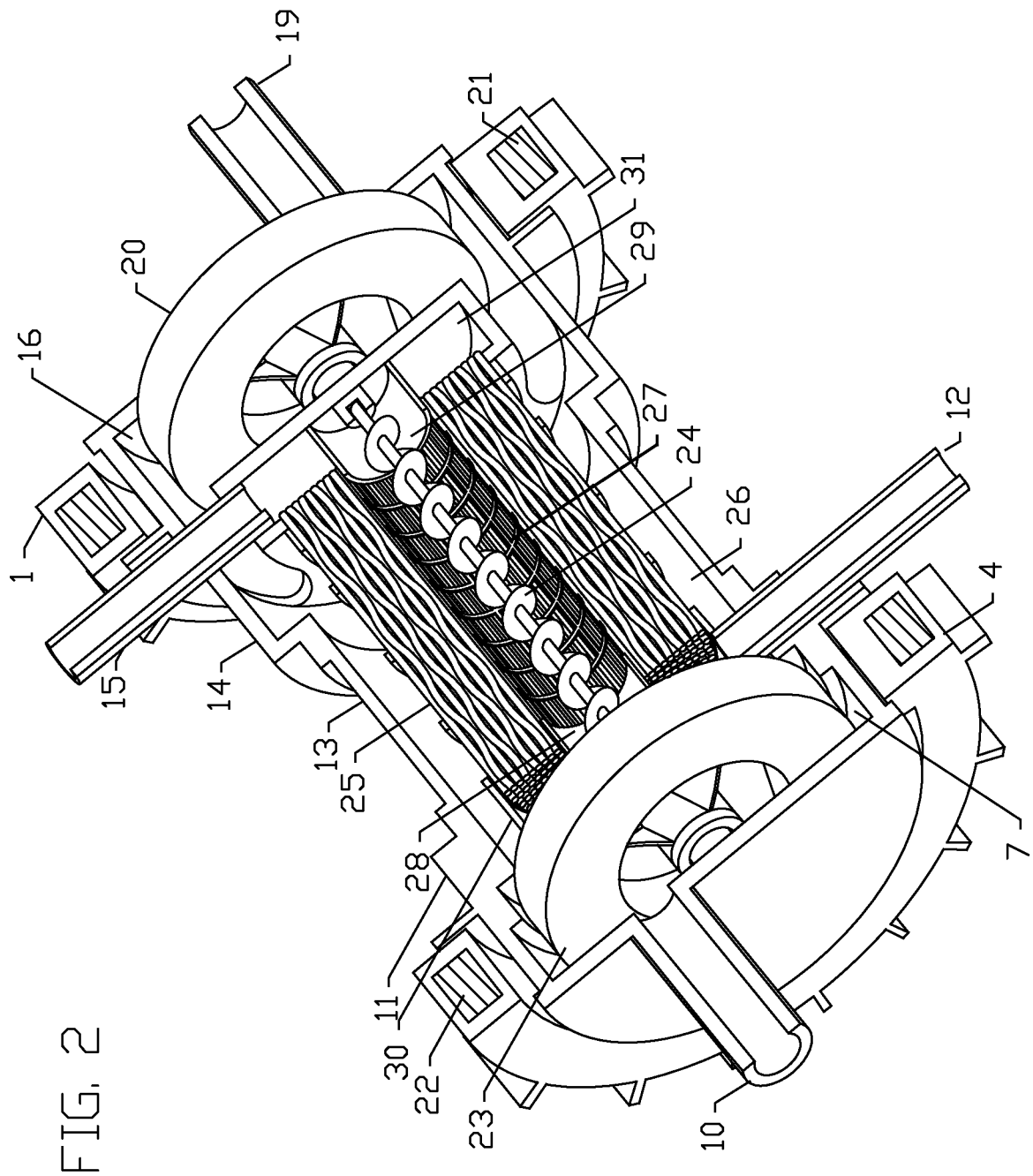
FIG. 2 represents a schematic three-dimensional exposed cut-out view of the integrated motorized hemodialyzer.

FIG. 2 shows a schematic three-dimensional exposed cut-out view of the integrated motorized hemodialyzer. the integrated motorized hemodialyzer is provided in a cylindrical configuration, which comprises a proximal dialyzer compartment, the mid tubular dialyzer compartment, and a distal dialyzer compartment. The proximal dialyzer compartment comprises the dialysate inlet subcompartment 7 distally adjoining an outer coaxial tubular cylinder 30 of the blood outlet subcompartment which is coaxially located in the proximal portion 11 of the mid tubular dialyzer compartment 13. The proximal portion 11 of the mid tubular dialyzer compartment 13 adjoins a distal portion of the dialysate inlet subcompartment 7 proximally. The distal dialyzer compartment comprises the dialysate outlet subcompartment 14 & 16 proximally adjoining the blood inlet subcompartment 31 which is coaxially disposed inside the proximal portion 14 of the dialysate outlet subcompartment.

The proximal portion 14 of the dialysate outlet subcompartment proximally adjoins a distal portion of the mid tubular dialyzer compartment 13. A packed bundle of hollow fibers 25 in a doughnut configuration on a radial cross-section is coaxially disposed inside the mid tubular dialyzer compartment 13. A proximal portion of the packed bundle of the hollow fibers 25 is fixedly encased by the outer coaxial tubular cylinder 30. A distal portion of the packed bundle of the hollow fibers 25 is fixedly encased by the blood inlet subcompartment 31. The packed bundle of the hollow fibers 25 comprises an open central tubular column 27 coaxially disposed along a longitudinal axis of said packed bundle of said hollow fibers 25. The open central tubular column 27 is sealably connected to the dialysate inlet subcompartment 7 via a proximal inner coaxial tubular cylinder 28 at the proximal portion of the packed bundle of the hollow fibers 25. The open central tubular column 27 is fixedly sealed with a dead end by a distal inner coaxial tubular cylinder 29 coaxially and fixedly disposed inside the blood inlet subcompartment 31.

Dialysate delivered via the dialysate intake tube 10 into the dialysate inlet subcompartment 7 is rotatably propelled by a dialysate inlet internal rotor 23 having an axial spiral flow converter into the open central tubular column 27 of the packed bundle of the hollow fibers 25. The dialysate inlet internal rotor 23 is electrically rotatable by the dialysate inlet external stator 4 which comprises a plurality of electric windings 22 fixedly encased in a cylindrical rim of said dialysate inlet external stator 4. The dialysate inside the open central tubular column 27 is then centrifugally spread across the packed bundle of the hollow fibers 25 into an outer circumferential space 26 by a longitudinal spiral blade 24 of the axial spiral flow converter slidably disposed inside the open central tubular column 27. The dialysate then is rotatably drained out through the dialysate out tube 19 from the outer circumferential space 26 by a dialysate outlet internal rotor 20 rotatably housed in the distal portion 16 of the dialysate outlet subcompartment via the proximal portion 14 of the dialysate outlet subcompartment. The dialysate outlet internal rotor 20 is electrically rotatable by the dialysate outlet external stator 1 which comprises a plurality of electric windings 21 fixedly encased in a cylindrical rim of said dialysate outlet external stator 1. Blood delivered via the blood intake tube 15 into the blood inlet subcompartment 31 of the distal dialyzer compartment moves through the packed bundle of the hollow fibers 25 to the blood outlet subcompartment of the proximal dialyzer compartment. The blood then flows out via the blood output tube 12. Thus, a countercurrent flow configuration is established between dialysate flow and blood flow.

Figure 3:
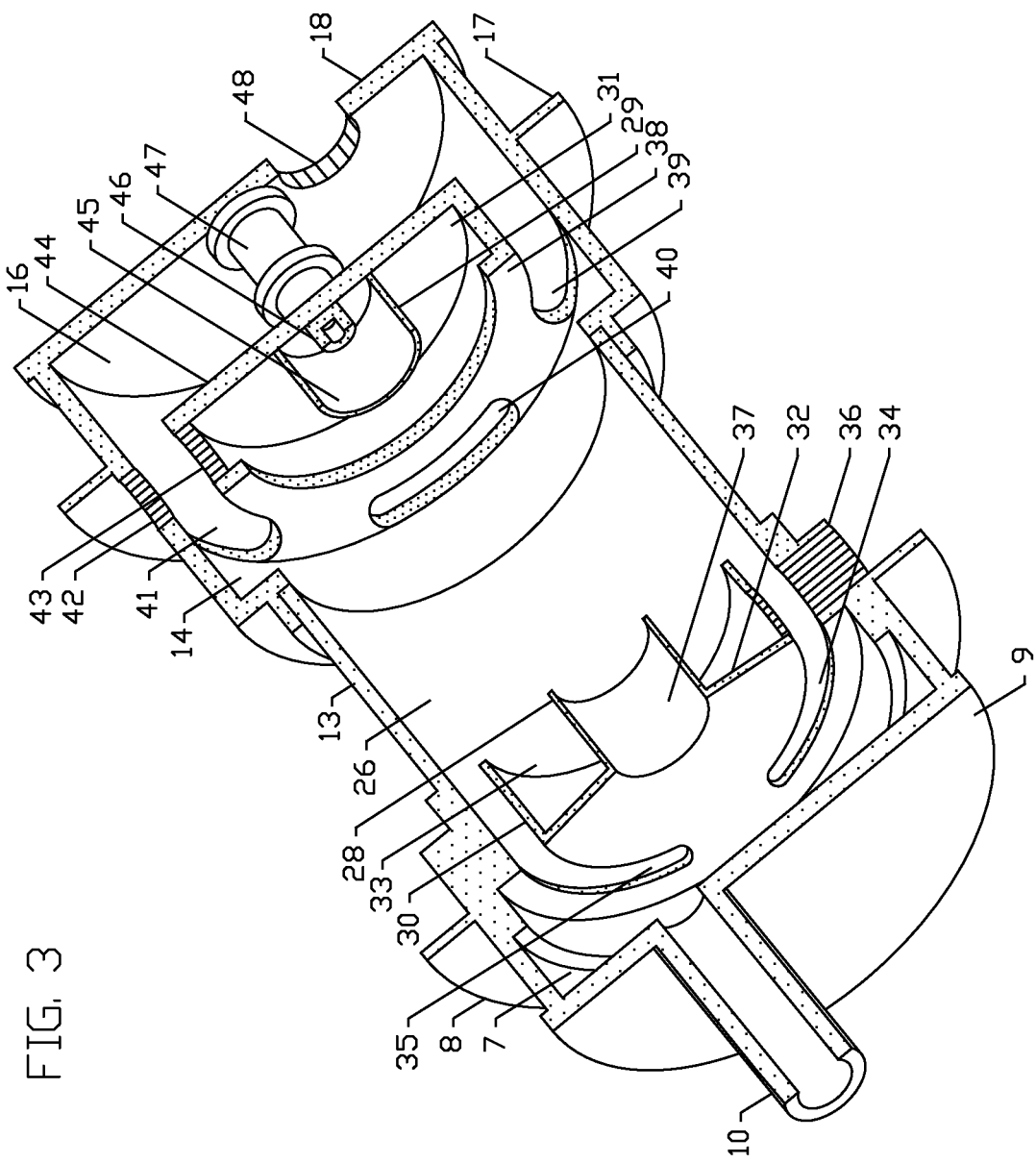
FIG. 3 illustrates a schematic three-dimensional exposed cut-out view of an outer shell of the cylindrical hemodialyzer.
Figure 7A:
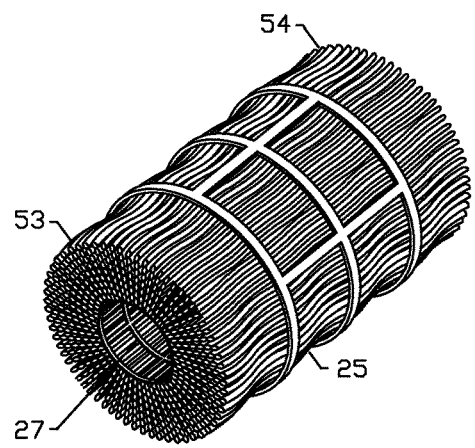
FIGS. 7A-7D show a schematic view of individual components of a packed bundle of hollow fibers.
Figure 7B:
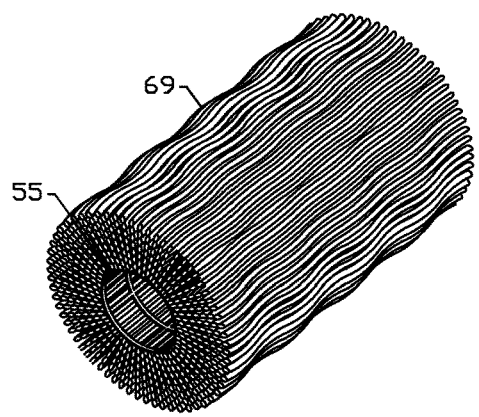
Figure 7C:
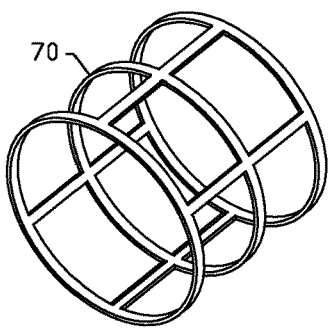
Figure 7D:
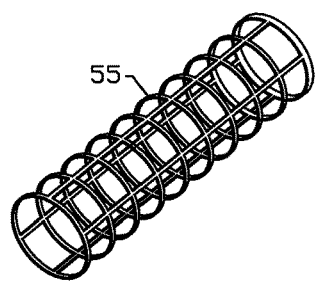

FIG. 3 illustrates a schematic three-dimensional exposed cut-out view of an outer shell of the cylindrical hemodialyzer comprising the dialysate inlet subcompartment 7, the blood outlet subcompartment 33, the mid tubular dialyzer compartment 13, the proximal portion 14 of the dialysate outlet subcompartment, the distal portion 16 of the dialysate outlet subcompartment, and the blood inlet subcompartment 31. Referring to FIG. 2, the dialysate intake tube 10 adjoins and opens to the dialysate inlet subcompartment 7 through the proximal radial wall 9, and the blood output tube 12 adjoins and opens to the blood outlet subcompartment 33 through a conduit 36. The dialysate inlet subcompartment 7 comprises an upper radial wall 32 having a central opening distally adjoining the proximal inner coaxial tubular cylinder 28 and a plurality of upper curvilinear fenestrations 34-35 located around a perimeter of said upper radial wall 32. The plurality of the upper curvilinear fenestrations 34-35 is configured to serve as conduit for recirculating the dialysate from the outer circumferential space 26 back to the dialysate inlet subcompartment 7. The outer coaxial tubular cylinder 30 protrudably adjoins an undersurface of the upper radial wall 32, wherein the outer coaxial tubular cylinder 30 coaxially encircles the proximal inner coaxial tubular cylinder 28 in a doughnut configuration. The proximal inner coaxial tubular cylinder 28 concentrically divides the blood outlet subcompartment 33 into an outer tubular columnar space and an inner tubular columnar space 37. Blood only resides in the outer tubular columnar space. The inner tubular columnar space 37 is only filled in with the dialysate. The upper radial wall 32 of the dialysate inlet subcompartment 7 is leveled with the proximal circumferential wing 8. The mid tubular dialyzer compartment 13 is provided in an open tubular configuration having the outer circumferential space 26.

The distal dialyzer compartment comprises the dialysate outlet subcompartment 14 & 16 and the blood inlet subcompartment 31. The dialysate outlet subcompartment is divided into the proximal portion 14 and the distal portion 16 of said dialysate outlet subcompartment by a lower radial wall 38, wherein the lower radial wall 38 is configured proximally with a wide tubular opening in a center and a plurality of lower curvilinear fenestrations 39-41 located around a perimeter of said lower radial wall 38. Referring to FIG. 2, the wide tubular opening in the center of the lower radial wall 38 is configured to sealably encircle an outer peripheral layer of the distal portion of the packed bundle of the hollow fibers 25. The plurality of the lower curvilinear fenestrations 39-41 is configured to serve as conduit for the dialysate flowing from the proximal portion 14 to the distal portion 16 of the dialysate outlet subcompartment. Referring to FIG. 2, the dialysate output tube 19 adjoins and opens to the distal portion 16 of the dialysate outlet subcompartment through an opening 48 disposed through the distal radial wall 18, and the blood intake tube 15 adjoins and opens to the blood inlet subcompartment 31 through an opening 42 on a tubular sidewall of the dialysate outlet subcompartment and an opening 43 on a tubular sidewall of the blood inlet subcompartment 31. The blood inlet subcompartment 31 comprises a top radial wall 44, the distal inner coaxial tubular cylinder 29 protrudably adjoining an undersurface of the top radial wall 44, and the tubular sidewall having the circular opening 43 of the blood intake tube 15. The distal inner coaxial tubular cylinder 29 concentrically divides the blood inlet subcompartment 31 into an outer tubular columnar space and an inner tubular columnar space 45. Blood only resides in the outer tubular columnar space. The inner tubular columnar space 45 is only filled in with the dialysate. Referring to FIG. 2, the distal inner coaxial tubular cylinder 29 is configured to be fixedly inserted into the distal portion of the open central tubular column 27 of the packed bundle of the hollow fibers 25. Referring to FIG. 2, a tubular flange 46 is disposed at a center of the undersurface of the top radial wall 44 of the blood inlet subcompartment 31, and is configured to slidably and axially encircle a distal portion of the longitudinal spiral blade 24. In the distal portion 16 of the dialysate outlet subcompartment, there is provided an axial cylindrical rod 47 fixedly adjoining an upper surface of the top radial wall 44 and an undersurface of the distal radial wall 18. Referring to FIG. 2, the axial cylindrical rod is disposed along the longitudinal axis of the cylindrical hemodialyzer, and is configured to rotatably anchor the dialysate outlet internal rotor 20. Similarly, there is provided an axial cylindrical rod for the dialysate inlet internal rotor 23 (not shown) in the dialysate inlet subcompartment 7. The distal circumferential wing 17 is leveled with the top radial wall 44 of the blood inlet subcompartment 31.

FIG. 4A depicts a schematic example of the dialysate outlet internal rotor 20 comprising the second helical spiral 50 fixedly attached to an inner circumferential surface 49 of said dialysate outlet internal rotor 20. The helical spiral comprises a plurality of helical blades radially attached to a rotor center 51 provided in a tubular configuration. The axial cylindrical rod 47 of the distal portion 16 of the dialysate outlet subcompartment shown in FIG. 4B is configured to rotatably slide in and provide axial rotatory support for the rotor center 51 of the dialysate outlet internal rotor 20 housed in the distal portion 16. The axial cylindrical rod 52 disposed in the dialysate inlet subcompartment 7 is fixedly and coaxially attached to an undersurface of the proximal radial wall 9, and is configured to rotatably slide in and provide axial rotatory support for a rotor center 58 of the dialysate inlet internal rotor 23 shown in FIG. 4D, wherein the dialysate inlet internal rotor 23 is housed in the dialysate inlet subcompartment 7. The rotor center 58 is a part of a first helical spiral 57 which is fixedly attached to an inner circumferential surface 56 of the dialysate inlet internal rotor 23. The first helical spiral 57 comprises a plurality of helical blades radially attached to the rotor center 58 provided in a tubular configuration. Shown in FIG. 4D, the axial spiral flow converter comprises the first helical spiral 57 as a head portion fixedly connected to the longitudinal spiral blade 24 as a stem portion. A distal tip 59 of the longitudinal spiral blade 24 is configured to rotatably slide in the tubular flange 46 shown in FIG. 4B, wherein the tubular flange 46 is disposed at the center of the undersurface of the top radial wall 44 of the blood inlet subcompartment 31.

The packed bundle of the hollow fibers 25 shown in FIG. 4C is configured to be coaxially placed in the outer circumferential space 26 of the mid tubular dialyzer compartment 13. The proximal portion 53 of the packed bundle of the hollow fibers 25 shown in FIG. 4C is configured to be sealably encircled by the outer coaxial tubular cylinder 30 of the blood outlet subcompartment 33. The proximal inner coaxial tubular cylinder 28 of the blood outlet subcompartment 33 is configured to be sealably inserted in a proximal portion of the open central tubular column 27 of the packed bundle of the hollow fibers 25 shown in FIG. 4C. The open central tubular column 27 communicates in an open configuration with the dialysate inlet subcompartment via the inner tubular columnar space 37. In a similar configuration, the distal portion 54 of the packed bundle of the hollow fibers 25 shown in FIG. 4C is configured to be sealably encircled by the wide tubular opening of the lower radial wall 38 of the blood inlet subcompartment 31 shown in FIG. 4B. The distal inner coaxial tubular cylinder 29 of the blood inlet subcompartment 31 shown in FIG. 4B is configured to be sealably inserted in a distal portion (not shown) of the open central tubular column 27 of the packed bundle of the hollow fibers 25 shown in FIG. 4C. The longitudinal spiral blade 24 is configured to be slidably inserted in the open central tubular column 27 of the packed bundle of the hollow fibers 25 shown in FIG. 4C.

FIG. 5A shows a schematic illustration of the dialysate inlet external stator 4 of the dialysate inlet motor, comprising the outer pin 6 and the inner pin 5 for the air cooling. The dialysate inlet external stator 4 is provided in a cylindrical configuration, and comprises a plurality of electric windings 60 with each having wound electric coil 61 arranged in a circumferential configuration shown in FIG. 5B. Referring to FIG. 2, the dialysate inlet external stator 4 disposed outside the tubular cylinder is configured to coaxially encircle the dialysate inlet internal rotor 23 disposed inside the tubular cylinder having the longitudinal spiral blade 24 shown in FIG. 5C. The dialysate outlet external stator 1 shown in FIG. 1 is provided in exactly the same configuration as that of the dialysate inlet external stator 4. Shown in FIGS. 6A-6C, the dialysate inlet internal rotor 23 comprises a plurality of blocks of permanent magnet 62 arranged in a circumferential configuration disposed inside said dialysate inlet internal rotor 23. The first helical spiral 57 comprises the plurality of the helical blades 63 helically attached to the rotor center 58 having a tubular opening 64. An outer perimeter of the plurality of the helical blades 63 is configured to be fixedly attached to the inner surface 56 of the cylindrical rim. The first helical spiral 57 is distally connected to the longitudinal spiral blade 24 having the distal tip 59, wherein a connecting point between the first helical spiral 57 and the longitudinal spiral blade 24 is reinforced by a flange 65. FIGS. 6D-6F illustrate a schematic example of the dialysate outlet internal rotor 20 comprising a plurality of blocks of permanent magnet 66 arranged in a circumferential configuration disposed inside said dialysate outlet internal rotor 20. The second helical spiral 50 comprises the plurality of the helical blades 67 helically attached to the rotor center 51 having a tubular opening 68. An outer perimeter of the plurality of the helical blades 67 is configured to be fixedly attached to the inner surface 49 of the cylindrical rim.

FIGS. 7A-7D show the packed bundle of the hollow fibers 25 comprising individual hollow fibers concentrically stacked up from around a first set of resiliently stiff string harness 55 abuttingly disposed on a perimeter of the open central tubular column 27 up to an outer surface 69 of said packed bundle of the hollow fibers 25, thus forming a cylindrical column in a doughnut configuration. The first set of resiliently stiff string harness 55 in a tubular configuration provides said open central tubular column 27 with a structural strength so as to avoid inward collapse of the open central tubular column. A second set of elastomeric string harness 70 in a tubular configuration is provided on the outer surface 69 of a peripheral layer of the packed bundle of the hollow fibers 25 to securely tie up said packed bundle of the hollow fibers 25.

Figure 8:
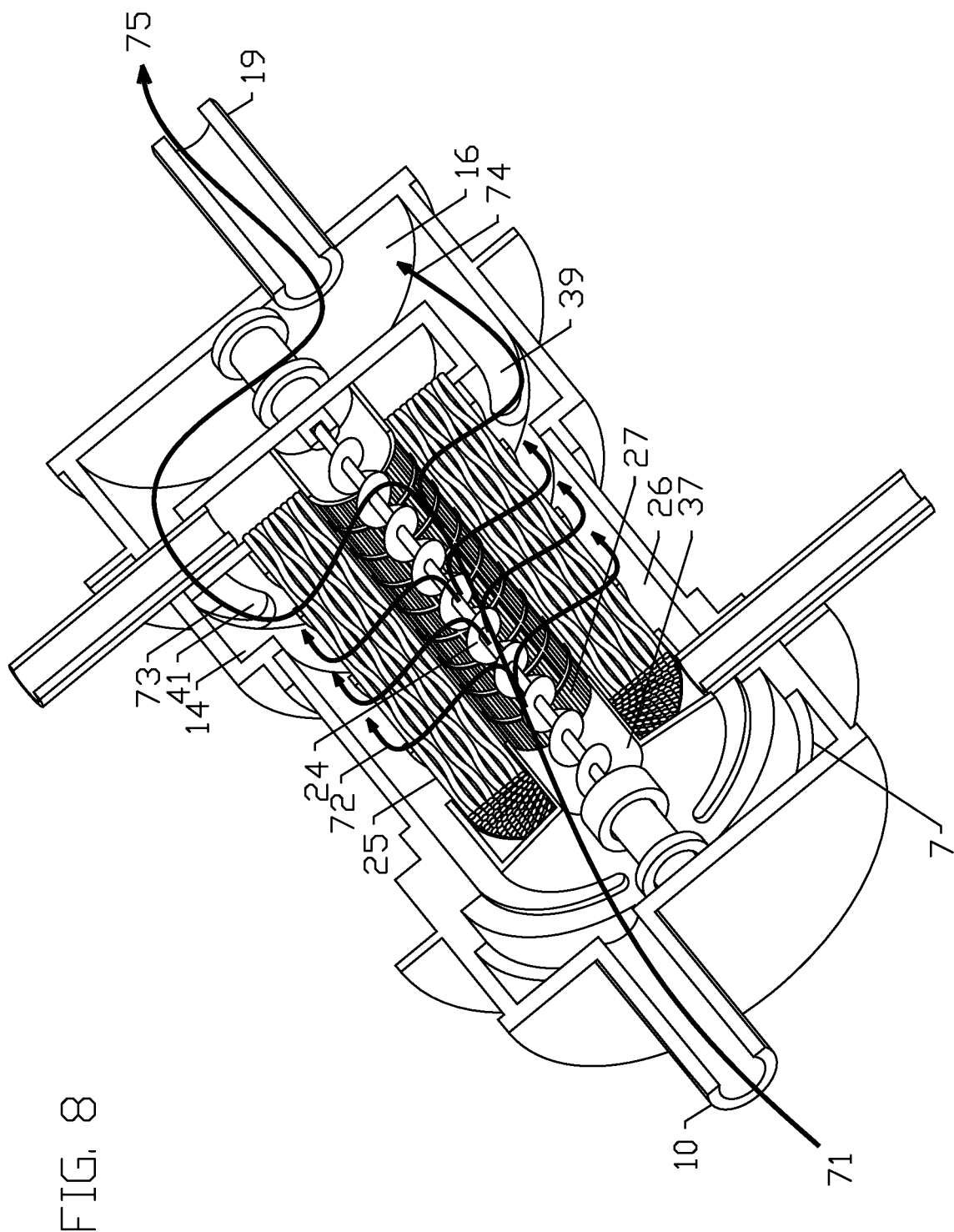
FIG. 8 shows a schematic illustration of dialysate flow in a proximal-to-distal direction.
Figure 9:
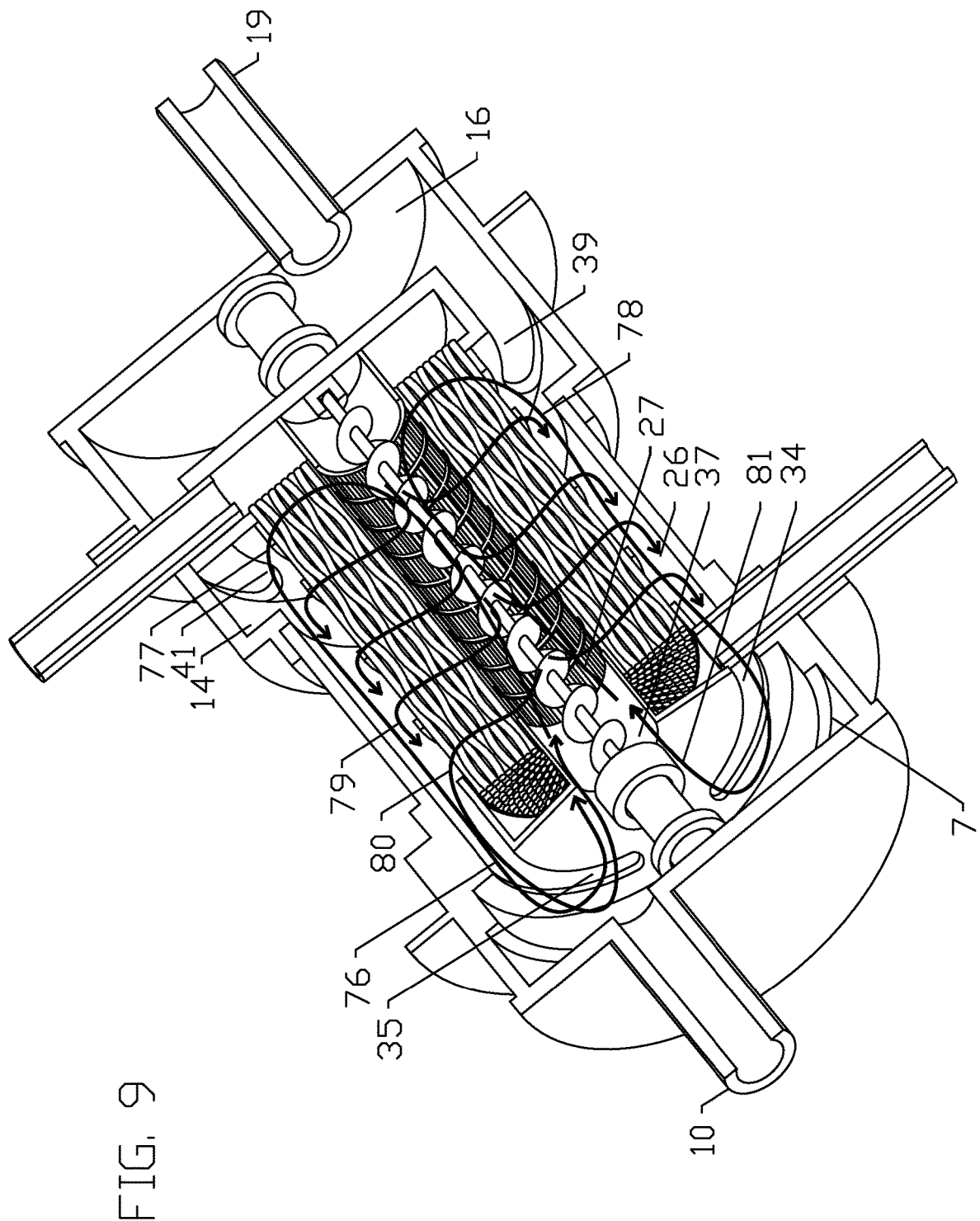
FIG. 9 shows a schematic illustration of recirculating dialysate flow.
Figure 10:
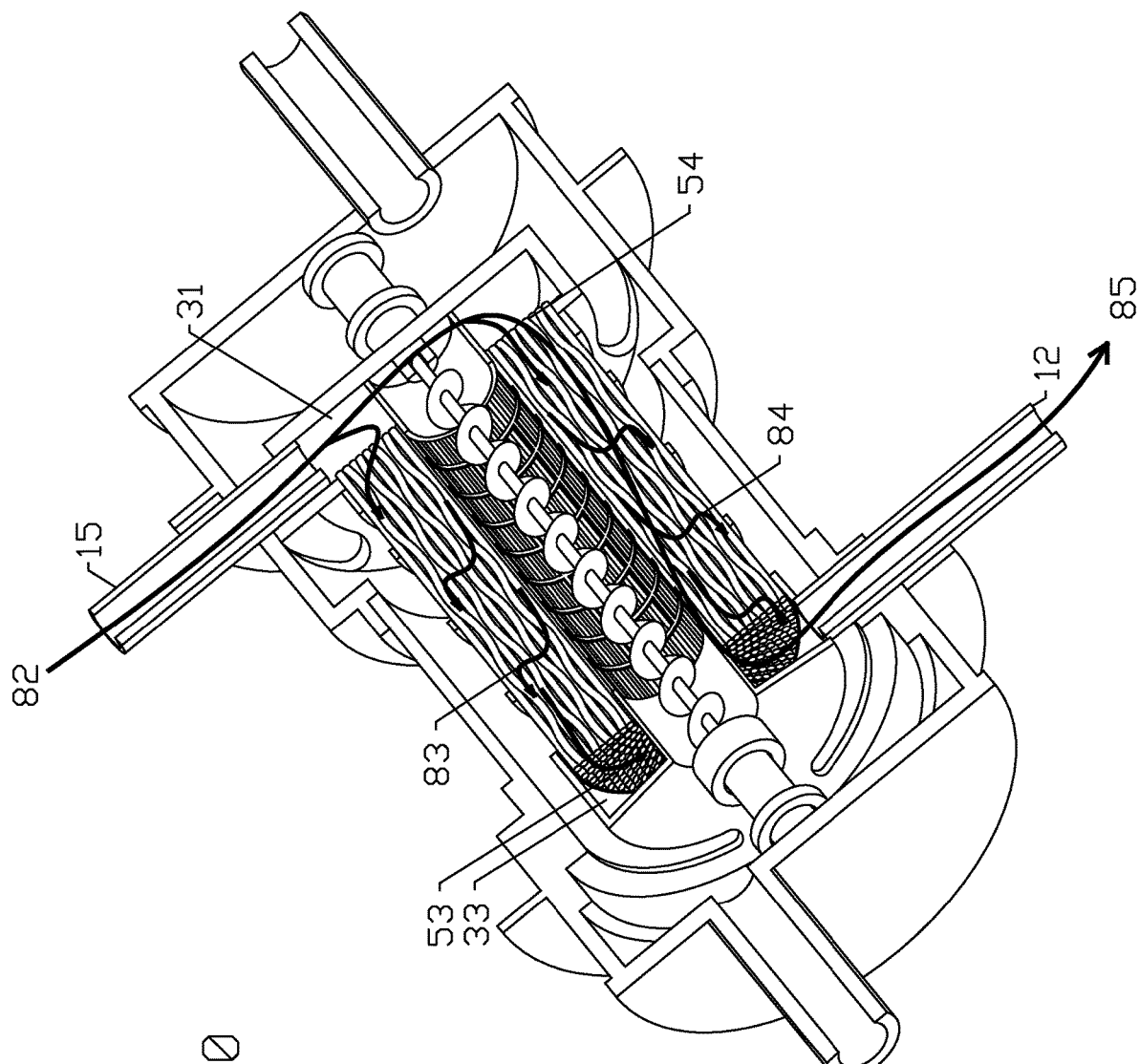
FIG. 10 shows a schematic illustration of blood flow in a countercurrent direction to the dialysate flow.

FIG. 8 shows a schematic view of a dialysate flow in a proximal-to-distal direction. An incoming dialysate 71 through the dialysate intake tube 10 rotatably is propelled in the open central tubular column 27 from the dialysate inlet subcompartment 7 via the inner tubular columnar space 37. The longitudinal spiral blade 24 of the axial spiral flow converter rotatably pushes the dialysate in a centrifugal direction 72 across the packed bundle of the hollow fibers 25 into the outer circumferential space 26. The dialysate collected in the proximal portion 14 of the dialysate outlet subcompartment then flows through the lower curvilinear fenestrations 39 & 41 (73 & 74, respectively) into the distal portion 16 of the dialysate outlet subcompartment. The dialysate (75) then is drained out through the dialysate output tube 19. FIG. 9 illustrates a schematic example of a recirculating dialysate flow. Intake of a fresh dialysate through the dialysate intake tube 10 is halted, and the distal portion 16 of the dialysate outlet subcompartment no longer accepts the dialysate from the proximal portion 14 through the lower curvilinear fenestrations 39 & 41 in this diagram. The dialysate (76) in the dialysate inlet subcompartment 7 is propelled into the open central tubular column 27. The longitudinal spiral blade 24 of the axial spiral flow converter rotatably pushes the dialysate in the centrifugal direction across the packed bundle of the hollow fibers 25 into the outer circumferential space 26. The dialysate in the outer circumferential space 26 and the dialysate collected in the proximal portion 14 of the dialysate outlet subcompartment then are propelled by the dialysate inlet internal rotor having the helical spiral shown in FIG. 2 in a recirculating direction 78-80 back to the dialysate inlet subcompartment 7 through the upper curvilinear fenestrations 34-35. The recirculated dialysate (81) in the dialysate inlet subcompartment 7 is propelled again into the open central tubular column 27, thereby establishing endless loop of recirculation as long as the dialysate inlet internal rotor having the helical spiral shown in FIG. 2 continues to rotate. In FIG. 10, incoming blood 82 flows from the blood intake tube 15 into the blood inlet subcompartment 31, which then goes through the packed bundle of the hollow fibers 25 from the proximal portion 54 to the distal portion 53 of the said packed bundle of the hollow fibers 25 (83-84) disposed inside the mid tubular dialyzer compartment 13 to the blood outlet subcompartment 33. It then flows out (85) through the blood output tube 12.

Figure 11A:
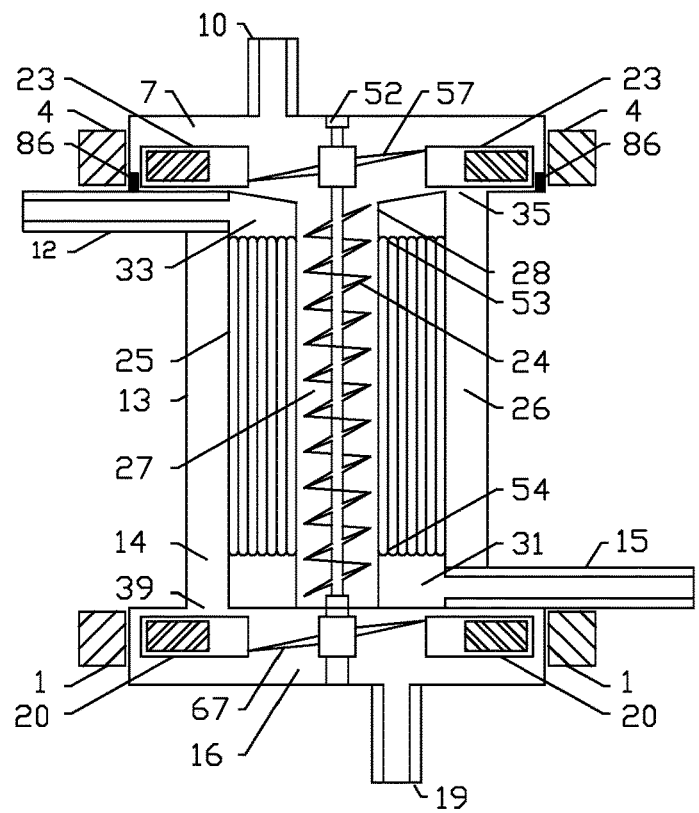
FIG. 11 depicts a two-dimensional view of the integrated motorized hemodialyzer.

FIG. 11A depicts a two-dimensional view of the integrated motorized hemodialyzer. the integrated motorized hemodialyzer has a blood compartment comprising the blood intake tube 15, the blood inlet subcompartment 31, the packed bundle of the hollow fibers 25, the blood outlet subcompartment blood outlet subcompartment 33, and the blood output tube 12. Dialysate flows from the dialysate intake tube 10 into the dialysate inlet subcompartment 7, which then is propelled into the open central tubular column 27 of the packed bundle of the hollow fibers 25 by the dialysate inlet internal rotor 23 having the first helical spiral 57. The dialysate inlet internal rotor 23 is electrically rotated by the dialysate inlet external stator 4. The dialysate then is centrifugally spread across the packed bundle of the hollow fibers 25 to the outer circumferential space 26 by the longitudinal spiral blade 24 of the axial spiral flow converter rotated by the first helical spiral 57. The outer circumferential space 26 is provided between the outer surface of the packed bundle of the hollow fibers 25 and the mid tubular dialyzer compartment 1. The dialysate in the outer circumferential space 26 is collected through the lower curvilinear fenestrations 39 into the distal portion 16 of the dialysate outlet subcompartment from which the dialysate is propelled out through the dialysate output tube 19 by the dialysate outlet internal rotor 20 having the second helical spiral 67. A lower circumferential rim 86 is disposed on an inner surface of a tubular cylinder of the dialysate inlet subcompartment 7 in a configuration that said lower circumferential rim 86 allows the dialysate inlet internal rotor 23 to get engaged with/disengaged from said lower circumferential rim 86 by downward/upward axial moving of said dialysate inlet internal rotor 23, respectively.

Figure 11B:
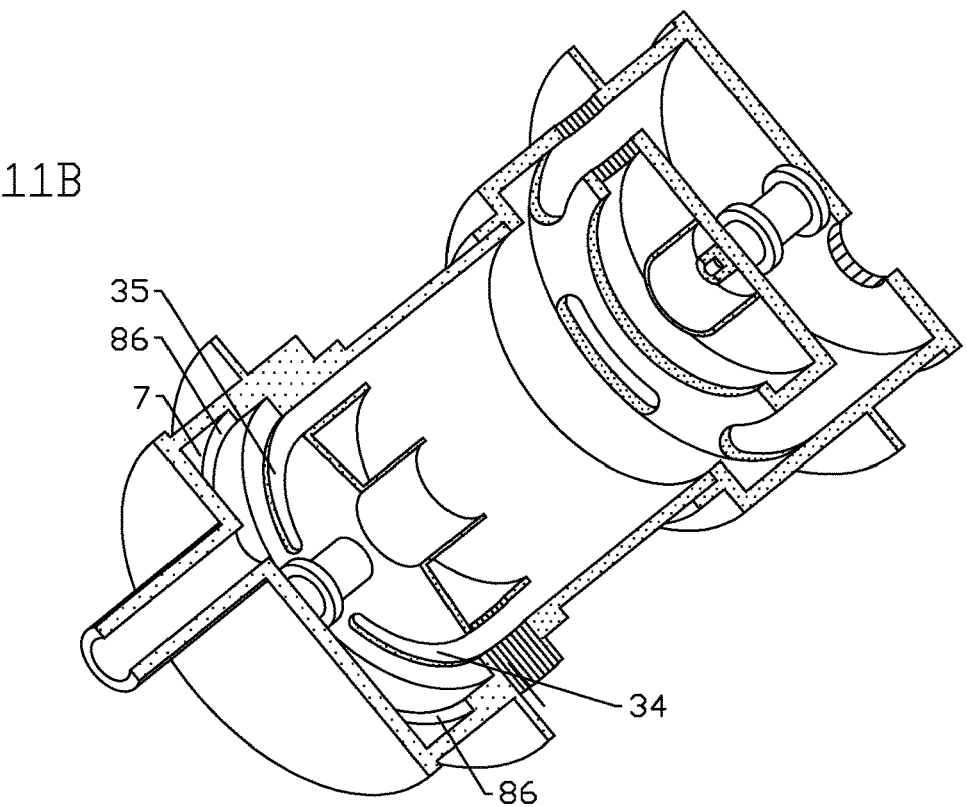

The dialysate outlet internal rotor 20 is electrically rotated by the dialysate outlet external stator 1. A motorized dialysate compartment of the integrated motorized hemodialyzer therefore comprises the dialysate intake tube 10, the dialysate inlet subcompartment 7, the open central tubular column 27 of the packed bundle of the hollow fibers 25 sealably connected to the dialysate inlet subcompartment 7 by the proximal inner coaxial tubular cylinder 28, the outer circumferential space 26 provided between the outer surface of the packed bundle of the hollow fibers 25 and the mid tubular dialyzer compartment 1, the dialysate outlet subcompartment 14 & 16, and the dialysate output tube 19. The outer circumferential space 26 is communicated with the dialysate inlet subcompartment 7 through 35 for on-demand recirculation of the dialysate. The blood compartment and the motorized dialysate compartment are separated and not directly communicated with each other except through a membrane of the individual hollow fibers of the packed bundle of the hollow fibers 25. FIG. 11B shows a schematic exposed three dimensional view of the lower circumferential rim 86 in the dialysate inlet subcompartment 7 and the upper curvilinear fenestrations 34-35.

Figure 12:
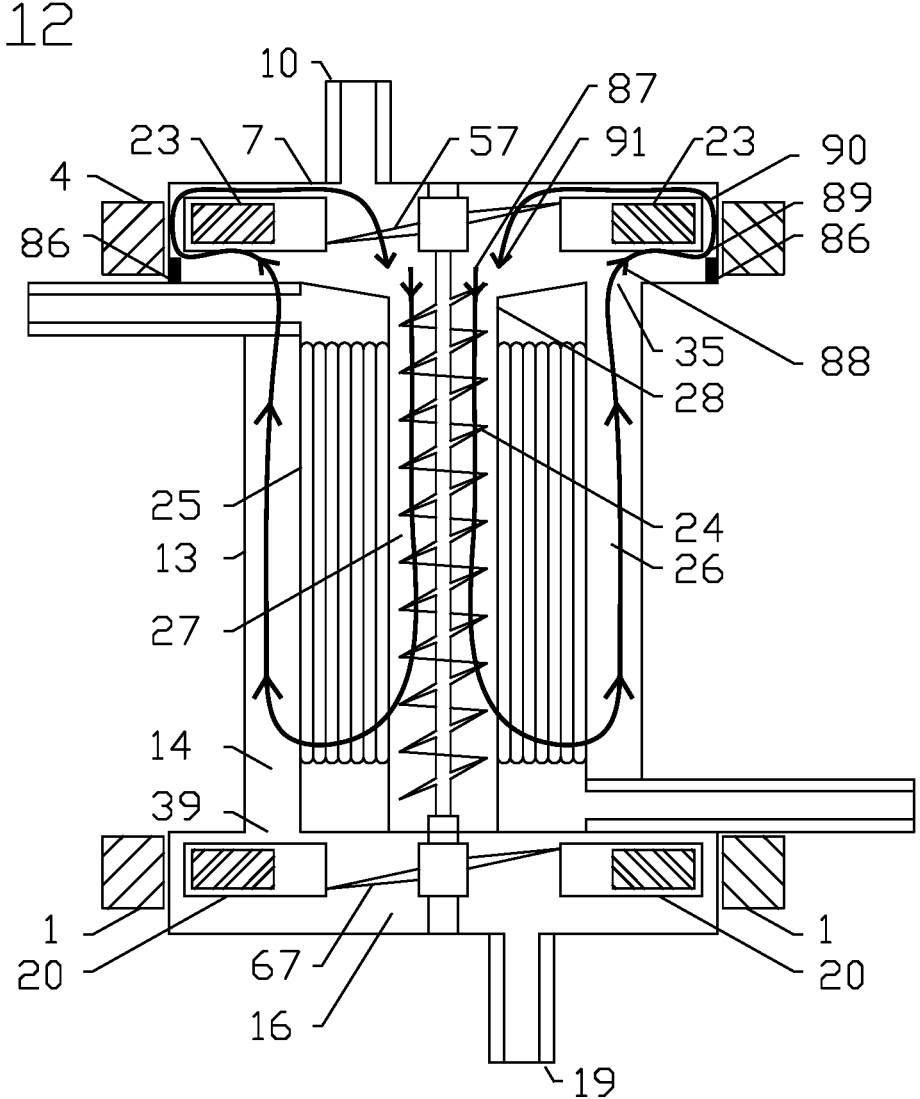
FIG. 12 shows an uplifting of a dialysate inlet internal rotor coincided with opening up a channel for the recirculating dialysate flow.

FIG. 12 shows a two-dimensional view of the integrated motorized hemodialyzer in a recirculating flow mode of the dialysate. The dialysate outlet motor having the dialysate outlet external stator 1 and the dialysate outlet internal rotor 20 with the central helical spiral 67 stays halted inside the distal portion 16 of the dialysate outlet subcompartment, which stops an out-flow of the dialysate through the dialysate output tube 19. Under this condition, ongoing rotation of the dialysate inlet motor comprising the dialysate inlet external stator 4 and the dialysate inlet internal rotor 23 with the central helical spiral 57 pushes the dialysate from the dialysate intake tube 10 in the dialysate inlet subcompartment 7 in an axial direction 87 to the open central tubular column 27 of the packed bundle of the hollow fibers 25. The dialysate then is centrifugally spread across the packed bundle of the hollow fibers 25 into the outer circumferential space 26 inside the mid tubular dialyzer compartment 13 by the longitudinal spiral blade 24 attached to the central helical spiral 57 of the dialysate inlet internal rotor 23. As the dialysate outlet motor stays stopped rotating, the dialysate is not allowed to flow into the proximal portion 14 of the dialysate outlet subcompartment and through the lower curvilinear fenestrations 39 to the distal portion 16 of the dialysate outlet subcompartment. Instead the dialysate inside the outer circumferential space 26 is being pushed up through the upper curvilinear fenestrations 35 and uplifts (88) the dialysate inlet internal rotor 23 out of the lower circumferential rim 86 inside the dialysate inlet subcompartment 7. The uplifted dialysate inlet internal rotor 23 stays open by the dialysate (88) in a way to allow the dialysate flow around (89-90) the uplifted dialysate inlet internal rotor 23. The dialysate then is sucked back (91) into the open central tubular column 27 via the proximal inner coaxial tubular cylinder 28 by the rotating central helical spiral 57, thereby establishing the recirculating flow mode of the dialysate.

It is to be understood that the aforementioned description of the apparatus is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. An integrated motorized hemodialyzer for hemodialysis, comprising:
   a blood compartment comprising a packed bundle of hollow fibers in a doughnut configuration on a radial cross-section, wherein the blood compartment is concentrically enclosed in a motorized dialysate compartment;
   the motorized dialysate compartment, provided in a configuration of a compartmentalized tubular cylinder, wherein the motorized dialysate compartment comprises a dialysate inlet motor having an axial spiral flow converter and a dialysate outlet motor.

2. The integrated motorized hemodialyzer for hemodialysis according to claim 1, wherein the blood compartment further comprises:
   a blood inlet subcompartment disposed proximate to a dialysate outlet portion of the integrated motorized hemodialyzer;
   wherein the blood inlet subcompartment is concentrically divided into an outer tubular columnar space and an inner tubular columnar space by a distal an inner coaxial tubular cylinder of the blood inlet subcompartment;
   wherein the outer tubular columnar space of the blood inlet subcompartment fixedly encases a portion of the packed bundle of the hollow fibers disposed proximate to the blood inlet subcompartment;
   wherein the blood inlet subcompartment is connected to a blood intake tube; and
   wherein the blood inlet subcompartment is configured to transmit blood to the packed bundle of the hollow fibers.

3. The integrated motorized hemodialyzer for hemodialysis according to claim 1, wherein the blood compartment further comprises:
   a blood outlet subcompartment disposed proximate to a dialysate inlet portion of the integrated motorized hemodialyzer;
   wherein the blood outlet subcompartment is concentrically divided into an outer tubular columnar space and an inner tubular columnar space by an inner coaxial tubular cylinder of the blood outlet subcompartment;
   wherein the outer tubular columnar space of the blood outlet subcompartment fixedly encases a portion of the packed bundle of the hollow fibers disposed proximate to the blood outlet subcompartment;
   wherein the blood outlet subcompartment is connected to a blood output tube; and
   wherein the blood outlet subcompartment is configured to transmit the blood from the packed bundle of the hollow fibers to the blood output tube.

4. The integrated motorized hemodialyzer for hemodialysis according to claim 1, wherein the packed bundle of the hollow fibers further comprises:
   an outer circumferential layer of the packed bundle of the hollow fibers;
   wherein the outer circumferential layer is separated by >2 mm of a radial distance from an inner tubular surface of the motorized dialysate compartment.

5. The integrated motorized hemodialyzer for hemodialysis according to claim 1, wherein the packed bundle of the hollow fibers further comprises:
   an open central tubular column disposed thereof along a longitudinal axis of the packed bundle of the hollow fibers;
   wherein the open central tubular column is concentrically surrounded by stacked-up individual straight hollow fibers of the packed bundle of the hollow fibers;
   wherein a portion of the open central tubular column proximate to a blood outlet subcompartment is fixedly encircled by an inner coaxial tubular cylinder of the blood outlet subcompartment;
   wherein a portion of the open central tubular column proximate to a blood inlet subcompartment is fixedly encircled by an inner coaxial tubular cylinder of the blood inlet subcompartment; and
   wherein the open central tubular column is configured to receive dialysate from the inner coaxial tubular cylinder of the blood outlet subcompartment.

6. The integrated motorized hemodialyzer for hemodialysis according to claim 1, wherein the motorized dialysate compartment further comprises:
- a mid tubular dialyzer compartment comprising a cylindrical tube bordered proximally by an upper radial wall and distally by a lower radial wall;
- wherein the upper radial wall comprises a plurality of upper curvilinear fenestrations arranged proximate to a perimeter of the upper radial wall;
- wherein the lower radial wall comprises a plurality of lower curvilinear fenestrations arranged proximate to a perimeter of the lower radial wall; and
- wherein the mid tubular dialyzer compartment coaxially houses the packed bundle of the hollow fibers.

7. The integrated motorized hemodialyzer for hemodialysis according to claim 6, wherein the mid tubular dialyzer further comprises:
- a metallic ink coating fixedly applied to an outer surface of the mid tubular dialyzer;
- wherein the metallic ink coating comprises a particulated metal such as copper or aluminum; and
- wherein the metallic ink coating is configured to limit radiofrequency electromagnetic radiation from the dialysate inlet motor and the dialysate outlet motor to the blood compartment.

8. The integrated motorized hemodialyzer for hemodialysis according to claim 1, wherein the motorized dialysate compartment further comprises:
- a dialysate inlet subcompartment disposed proximate to a blood outlet subcompartment of the integrated motorized hemodialyzer;
- wherein the dialysate inlet subcompartment rotatably and coaxially encloses an internal rotor of the dialysate inlet motor; and
- wherein the dialysate inlet subcompartment is coaxially encircled by an external stator of the dialysate inlet motor.

9. The integrated motorized hemodialyzer for hemodialysis according to claim 8, wherein the dialysate inlet subcompartment further comprises:
- the dialysate inlet subcompartment distally adjoins and opens to an inner coaxial tubular cylinder of the blood outlet subcompartment;
- wherein the dialysate inlet subcompartment is distally open to an open central tubular column of a packed bundle of the hollow fibers via the inner coaxial tubular cylinder of the blood outlet subcompartment;
- wherein the dialysate inlet subcompartment is connected to a dialysate intake tube; and
- wherein the dialysate inlet subcompartment is configured to deliver the dialysate to the open central tubular column.

10. The integrated motorized hemodialyzer for hemodialysis according to claim 8, wherein the dialysate inlet subcompartment further comprises:
- the dialysate inlet subcompartment distally adjoins an upper radial wall of a mid tubular dialyzer compartment;
- wherein the dialysate inlet subcompartment is distally open to an outer circumferential space of the mid tubular dialyzer compartment via a plurality of upper curvilinear fenestrations of the upper radial wall;
- wherein the dialysate inlet subcompartment is configured to recirculate a dialysate from the outer circumferential space back to the dialysate inlet subcompartment.

11. The integrated motorized hemodialyzer for hemodialysis according to claim 8, wherein the dialysate inlet subcompartment further comprises:
- a lower circumferential rim circumferentially protruding from an inner surface of a tubular sidewall of the dialysate inlet subcompartment;
- wherein the lower circumferential rim is disposed thereof proximal to the upper radial wall; and
- wherein the lower circumferential rim slidably accommodates the internal rotor of the dialysate inlet motor disposed in the dialysate inlet subcompartment.

12. The integrated motorized hemodialyzer for hemodialysis according to claim 11, wherein the lower circumferential rim further comprises:
- the lower circumferential rim circumferentially protruding from an inner surface of a tubular sidewall of the dialysate inlet subcompartment;
- wherein a radial gap between an inner surface of the lower circumferential rim and an outer perimeter of the internal rotor of the dialysate inlet motor is equal to or greater than 2 mm; and
- wherein a height of the lower circumferential rim is shorter than a length of an axial movement of the internal rotor of the dialysate inlet motor inside the dialysate inlet subcompartment.

13. The integrated motorized hemodialyzer for hemodialysis according to claim 1, wherein the motorized dialysate compartment further comprises:
- an outer circumferential space of a mid tubular dialyzer compartment, disposed between an outer circumferential layer of the packed bundle of the hollow fibers and an inner tubular surface of the mid tubular dialyzer compartment;
- wherein the outer circumferential space proximally adjoins an upper radial wall of the mid tubular dialyzer compartment;
- wherein the outer circumferential space proximally opens to a dialysate inlet subcompartment through a plurality of upper curvilinear fenestrations of the upper radial wall of the mid tubular dialyzer compartment;
- wherein the outer circumferential space is configured to transmit dialysate from the outer circumferential space to the dialysate inlet subcompartment through the plurality of the upper curvilinear fenestrations.

14. The integrated motorized hemodialyzer for hemodialysis according to claim 13, wherein the outer circumferential space further comprises:
- the outer circumferential space distally adjoins a lower radial wall of the mid tubular dialyzer compartment;
- wherein the outer circumferential space distally opens to a dialysate outlet subcompartment through a plurality of lower curvilinear fenestrations of the lower radial wall of the mid tubular dialyzer compartment;
- wherein the outer circumferential space is configured to transmit the dialysate from the outer circumferential space to the dialysate outlet subcompartment through the plurality of the lower curvilinear fenestrations.

15. The integrated motorized hemodialyzer for hemodialysis according to claim 1, wherein the motorized dialysate compartment further comprises:
- a dialysate outlet subcompartment disposed proximate to a blood inlet portion of the integrated motorized hemodialyzer;
- wherein the dialysate outlet subcompartment rotatably and coaxially encloses an internal rotor of the dialysate outlet motor; and wherein the dialysate outlet subcompartment is coaxially encircled by an external stator of the dialysate outlet motor.

16. The integrated motorized hemodialyzer for hemodialysis according to claim 15, wherein the dialysate outlet subcompartment further comprises:
   the dialysate outlet subcompartment proximally adjoins and opens to an outer circumferential space of a mid tubular dialyzer compartment;
   wherein the dialysate outlet subcompartment is configured to collect a dialysate from the outer circumferential space through a plurality of lower curvilinear fenestrations of a lower radial wall of the mid tubular dialyzer compartment;
   wherein the dialysate outlet subcompartment is connected to a dialysate output tube; and
   wherein the dialysate outlet subcompartment is configured to drain out the dialysate through the dialysate output tube.

17. The integrated motorized hemodialyzer for hemodialysis according to claim 1, wherein the dialysate inlet motor comprises:
   an external stator of the dialysate inlet motor comprising a plurality of electric windings, wherein said external stator disposed thereof outside a dialysate inlet subcompartment is configured to electromagnetically rotate an internal rotor of the dialysate inlet motor in the dialysate inlet subcompartment; and
   an internal rotor of the dialysate inlet motor comprising a plurality of blocks of permanent magnet arranged in a cylindrical rim of said internal rotor, wherein said internal rotor comprises a proximal axial propeller of the axial spiral flow converter fixedly and coaxially attached to an inner surface of a cylindrical rim of said internal rotor, and wherein said internal rotor is configured to deliver the dialysate to an open central tubular column of the packed bundle of the hollow fibers.

18. The integrated motorized hemodialyzer for hemodialysis according to claim 17, wherein the dialysate inlet motor further comprises:
   the internal rotor of the dialysate inlet motor disposed thereof inside the dialysate inlet subcompartment;
   wherein said internal rotor is configured to move up and down along a longitudinal axis of the dialysate inlet subcompartment;
   wherein said internal rotor in a down configuration in the dialysate inlet subcompartment substantially blocks off a plurality of upper curvilinear fenestrations of an upper radial wall of a mid tubular dialyzer compartment; and
   wherein said internal rotor in an up configuration in the dialysate inlet subcompartment opens up the plurality of the upper curvilinear fenestrations.

19. The integrated motorized hemodialyzer for hemodialysis according to claim 1, wherein the dialysate outlet motor comprises:
   an external stator of the dialysate outlet motor comprising a plurality of electric windings, wherein said external stator disposed thereof outside a dialysate outlet subcompartment is configured to electromagnetically rotate an internal rotor of the dialysate outlet motor in the dialysate outlet subcompartment, and wherein said external stator is coaxially aligned with an external stator of the dialysate inlet motor;
   the internal rotor of the dialysate outlet motor comprising a plurality of blocks of permanent magnet arranged in a cylindrical rim of said internal rotor, wherein said internal rotor comprises a distal axial propeller fixedly and coaxially attached to an inner surface of a cylindrical rim of said internal rotor, and wherein said internal rotor is configured to rotatably drain out a dialysate from the dialysate outlet subcompartment through the dialysate output tube; and
   wherein said internal rotor is coaxially aligned with an internal rotor of the dialysate inlet motor.

20. The integrated motorized hemodialyzer for hemodialysis according to claim 1, wherein the axial spiral flow converter further comprises:
   a longitudinal spiral blade proximally and coaxially adjoining a proximal axial propeller comprising a set of rotary blades;
   the longitudinal spiral blade comprising a single spiral blade fixedly encircling a longitudinal shaft;
   wherein a distal tip of the longitudinal spiral blade is rotatably anchored inside an inner tubular columnar space of a blood inlet subcompartment;
   wherein the longitudinal spiral blade is coaxially disposed thereof inside open central tubular column of the packed bundle of the hollow fibers;
   wherein the longitudinal spiral blade is configured to coaxially rotate inside the open central tubular column;
   wherein the longitudinal spiral blade in a rotating configuration is configured to pull a dialysate in the open central tubular column from the dialysate inlet subcompartment; and
   wherein the longitudinal spiral blade in the rotating configuration is configured to centrifugally spread the dialysate in the open central tubular column across the packed bundle of the hollow fibers to an outer circumferential space of the motorized dialysate compartment.

* * * * *